US006740324B2

US 6,740,324 B2

(12) United States Patent
Schall et al.

(10) Patent No.: US 6,740,324 B2
(45) Date of Patent: May 25, 2004

(54) METHODS AND COMPOSITIONS USEFUL FOR STIMULATING AN IMMUNE RESPONSE

(75) Inventors: Thomas J. Schall, Menlo Park, CA (US); Mark E. T. Penfold, Mountain View, CA (US)

(73) Assignee: ChemoCentryx, Inc., San Carlos, CA (US)

( * ) Notice: Subject to any disclaimer, the term of this patent is extended or adjusted under 35 U.S.C. 154(b) by 11 days.

(21) Appl. No.: 10/061,943

(22) Filed: Feb. 1, 2002

(65) Prior Publication Data

US 2002/0176870 A1 Nov. 28, 2002

Related U.S. Application Data

(60) Provisional application No. 60/265,925, filed on Feb. 2, 2001.

(51) Int. Cl.[7] ................... A61K 39/245; A61K 39/295; C12N 15/869; C12N 7/01
(52) U.S. Cl. ................ 424/199.1; 424/230.1; 435/320.1; 435/235.1; 435/236
(58) Field of Search ............... 435/320.1, 235.1, 435/236; 424/199.1, 230.1, 813.2

(56) References Cited

U.S. PATENT DOCUMENTS

| | | | |
|---|---|---|---|
| 3,379,729 A | 4/1968 | Protiva et al. | |
| 5,529,771 A | 6/1996 | Hooks et al. | |
| 5,652,133 A | 7/1997 | Murphy | |
| 5,665,362 A | * 9/1997 | Inglis et al. | ............ 424/205.1 |
| 5,720,957 A | 2/1998 | Jones et al. | |
| 5,753,476 A | 5/1998 | Jones et al. | |
| 5,756,264 A | 5/1998 | Schwartz et al. | |
| 5,763,217 A | 6/1998 | Cynader et al. | |
| 5,824,318 A | 10/1998 | Mohr et al. | |
| 5,843,458 A | 12/1998 | Jones | |
| 5,846,806 A | 12/1998 | Jones et al. | |
| 5,866,136 A | 2/1999 | Ramshaw et al. | |
| 5,877,004 A | 3/1999 | Jones et al. | |
| 5,908,780 A | 6/1999 | Jones | |
| 5,939,320 A | 8/1999 | Littman et al. | |
| 5,948,775 A | 9/1999 | Koko et al. | |
| 5,965,697 A | 10/1999 | Czaplewski et al. | |
| 5,998,160 A | 12/1999 | Berens | |
| 6,028,169 A | 2/2000 | Kreider et al. | |
| 6,031,080 A | 2/2000 | Williams et al. | |
| 6,033,671 A | 3/2000 | Frueh et al. | |
| 6,034,102 A | 3/2000 | Aiello | |
| 6,051,375 A | 4/2000 | Rose et al. | |
| 6,051,428 A | 4/2000 | Fong et al. | |
| 6,150,132 A | 11/2000 | Wells et al. | |
| 6,420,121 B1 | 7/2002 | Nelson et al. | |

FOREIGN PATENT DOCUMENTS

| | | | |
|---|---|---|---|
| EP | 0277773 | * 10/1988 | ........... C12N/15/00 |
| WO | WO 94/11504 A1 | 5/1994 | |
| WO | WO 96/23068 A1 | 8/1996 | |
| WO | WO 98/02151 A2 | 1/1998 | |
| WO | WO 98/11073 A1 | 3/1998 | |
| WO | WO 99/00510 A1 | 1/1999 | |
| WO | WO 99/09178 A1 | 2/1999 | |
| WO | WO 99/27122 A1 | 6/1999 | |
| WO | WO 99/36562 A1 | 7/1999 | |
| WO | WO 99/36568 A2 | 7/1999 | |
| WO | WO 99/64172 A1 | 12/1999 | |
| WO | WO 00/00491 A1 | 1/2000 | |
| WO | WO 00/06203 A1 | 2/2000 | |
| WO | WO 00/11950 A1 | 3/2000 | |
| WO | WO 00/34494 A1 | 6/2000 | |
| WO | WO 02/17900 A2 | 3/2002 | |
| WO | WO 02/17969 A2 | 3/2002 | |
| WO | WO 02/18954 A2 | 3/2002 | |

OTHER PUBLICATIONS

Manning et al (Journal of Virological Methods 73:31–39, 1998).*

Ward, Stephen G., et al.; Chemokines and T Lymphocytes: More than an Attraction; *Immunity*; Jul. 1998; pp. 1–11; vol. 9.

Ziegler, Heike, et al.; A mouse Cytomegalovirus Glycoprotein Retains MHC Class I Complexes in the ERGIC/cis–Golgi Compartments; *Immunity*; Jan. 1997; pp. 57–66; vol. 6.

Beisser, Patrick S., et al.; The R33 G Protein–Coupled Receptor Gene of Rat Cytomegalovirus Plays an Essential Role in the Pathogenesis of Viral Infection; *Journal of Virology*; Mar. 1998; pp. 2352–2363; vol. 72, No. 3.

Beisser, Patrick S., et al.; Deletion of the R78 G Protein–Coupled Receptor Gene from Rat Cytomegalovirus Results in an Attenuated, Syncytium–inducing Mutant Strain; *Journal of Virology*; Sep. 1999; pp. 7218–7230; vol. 73, No. 9.

Beisser, P.S., et al.; Viral Chemokine Receptors and Chemokines in Human Cytomegalovirus Trafficking and Interaction with the Immune System; *Current Topics in Microbiology and Immunology*; 2002; pp. 203–234; vol. 269; Springer; Berlin, DE; XP008009472.

Billstrom, Marcella A. et al.; Intracellular Signaling by the Chemokine Receptor US28 during Human Cytomegalovirus Infection; *Journal of Virology*; Jul. 1998; pp. 5535–5544; vol. 72, No. 7.

(List continued on next page.)

*Primary Examiner*—Mary E. Mosher
(74) *Attorney, Agent, or Firm*—Townsend and Townsend and Crew LLP

(57) ABSTRACT

The invention provides compositions containing modified cytomegalovirus, and methods of using the compositions. In various embodiments, the modifications include adding a heterologous sequence encoding a non-viral chemokine element and/or immunogenic polypeptide, and/or disabling a viral dissemination gene.

70 Claims, 11 Drawing Sheets

OTHER PUBLICATIONS

Bodaghi, Bahram, et al.; Chemokine Sequestration by Viral Chemoreceptors as a Novel Viral Escape Strategy: Withdrawal of Chemokines from the Environment of Cytomegalovirus–infected Cells; *J. Exp. Med.*; Sep. 7, 1998, pp. 855–866; vol. 188, No. 5.

Borst, M.E., et al.; Development of a cytomegalovirus vector for somatic gene therapy; *Bone Marrow Transplantation*; 2000; pp. S80–S82; Supp. 2.

Cha, Tai–An, et al.; Human Cytomegalovirus Clinical Isolates Carry at Least 19 Genes Not Found in Laboratory Strains; *Journal of Virology*; Jan. 1996; pp. 78–83; vol. 70, No. 1.

Chee, M.S., et al.; Analysis of the Protein–Coding Content of the Sequence of Human Cytomegalovirus Strain AD169; *Current Topics in Microbiology and Immunology*; 1990; pp. 126–169; vol. 154.

Chee, M.S. et al.; Human cytomegalovirus encodes three G protein–coupled receptor homologues; *Nature*; Apr. 19, 1990; pp. 774–777; vol. 334.

Craigen, J.L., et al.; Human cytomegalovirus infection up–regulates interleukin-8 gene expression and stimulates neutrophil transendothelial migration; *Immunology*; 1997; pp. 138–145; vol. 92.

Davis–Poynter, Nicholas J., et al.; Masters of deception: A review of herpesvirus immune evasion strategies; *Immunology and Cell Biology*; 1996; pp. 513–522; vol. 74.

Davis–Poynter, Nicholas J., et al.; Identification and Characterization of a G Protein–Coupled Receptor Homolog Encoded by Murine Cytomegalovirus; *Journal of Virology*; Feb. 1997; pp. 1521–1529; vol. 71, No. 2.

Farrell, H.E., et al.; Inhibition of natural killer cells by a cytomegalovirus MHC class I homologue in vivo; *Nature*; Apr. 3, 1997; pp. 510–514; vol. 386.

Fleming, Peter, et al.; The Murine Cytomegalovirus Chemokine Homolog, m131/129, Is a Determinant of Viral Pathogenicity; *Journal of Virology*; Aug. 1999; pp. 6800–6809; vol. 73, No. 8.

Gao, Ji–Liang; et al.; Human Cytomegalovirus Open Reading Frame US28 Encodes a Functional β Chemokine Receptor; *The Journal of Biological Chemistry*, Nov. 18, 1994; pp. 28539–28542; vol. 269, No. 46.

GenBank Accession No: L20501; May 2, 1996.

GenBank Accession No.: AF073831; Jun. 23, 2000.

GenBank Accession No.: AF073832; Jun. 23, 2000.

GenBank Accession No.: AF073833; Jun. 23, 2000.

GenBank Accession No.: AF073834; Jun. 23, 2000.

GenBank Accession No.: AF073835; Jun. 23, 2000.

GenBank Accession No.: X17403; Feb. 10, 1999.

GenBank Accession No.: X53293; Dec. 1, 1992.

Gilbert, Mark J., et al.; Cytomegalovirus selectively blocks antigen processing and presentation of its immediate–early gene product; *Nature;* Oct. 24, 1996; pp. 720–722; vol. 383.

Gompels, U.A.; et al.; The DNA Sequence of Human Herpesvirus–6: Structure, Coding Content, and Genome Evolution; *Virology;* 1995; pp. 29–51; vol. 209.

Grundy, Jane E., et al.; Cytomegalovirus–Infected Endothelial Cells Recruit Neutrophils by the Secretion of C–X–C Chemokines and Transmit Virus by Direct Neutrophil–Endothelial Cell Contact and during Neutrophil Transendothelial Migration; *The Journal of Infectious Diseases;* 1998; pp. 1465–1467; vol. 177.

Harrison, Jeffrey K., et al.; Role for neuronally derived fractalkine in mediating interactions between neurons and CX3CR1–expressing microglia; *Proc. Natl. Acad. Sci. USA;* Sep. 1998; pp. 10896–10901; vol. 95.

Hirsch, Alec J., et al.; Human Cytomegalovirus Inhibits Transcription of the CC Chemokine MCP–1 Gene; *Journal of Virology;* Jan. 1999; pp. 404–410; vol. 73, No. 1.

Humar A., et al.; Elevated Serum Cytokines Are Associated with Cytomegalovirus Infection and Disease in Bone Marrow Transplant Recipients; *The Journal of Infectious Diseases;* 1999; pp. 484–488; vol. 179.

Isegawa, Yuji, et al.; Human Herpesvirus 6 Open Reading Frame U12 Encodes a Functional β–Chemokine Receptor; *Journal of Virology;* Jul. 1998; pp. 6104–6112; vol. 72, No. 7.

Kledal, Thomas N.; et al.; A Broad–Spectrum Chemokine Antagonist Encoded by Kaposi's Sarcoma–Associated Herpesvirus; *Science;* Sep. 12, 1997; pp. 1656–1659; vol. 277.

Kledal, Thomas N.; et al.; Selective recognition of the membrane–bound $CX_3C$ chemokine, fractalkine, by the human cytomegalovirus–encoded broad–spectrum receptor US28; *FEBS Letters;* 1998; pp. 209–214; vol. 441.

Kleijnen, Maurits F., et al.; A mouse cytomegalovirus glycoprotein, gp34, forms a complex with folded class I MHC molecules in the ER which is not retained but is transported to the cell surface; *EMBO Journal;* 1997, pp. 685–694; vol. 16, No. 4.

Kotenko, Sergei, et al.; Human cytomegalovirus harbors it own unique IL–10 homolog (cmvIL–10); Feb. 15, 2000, pp. 1695–1700, vol. 97, No. 4.

Kuhn, Donald, E., et al.; The Cytomegalovirus US28 Protein Binds Multiple CC Chemokines with High Affinity; *Biochemical and Biophysical Research Communications;* Jun. 6, 1995; pp. 325–330; vol. 211, No. 1.

Lockridge, Kristen M.; et al.; Primate Cytomegaloviruses Encode and Express an IL–10–like Protein; *Virology;* 2000; pp. 272–280; vol. 268.

Mahalingham, Surendran, et al.; Chemokines and chemokine receptors in infectious diseases; *Immunology and Cell Biology;* 1999; pp. 469–475; vol. 77.

Margulies, Barry J., et al.; Identification of the Human Cytomegalovirus G. Protein–Coupled Receptor Homologue Encoded by UL33 in Infected Cells and Enveloped Virus Particles; *Virology;* 1996; pp. 111–125; vol. 225.

Martin, W. John; Chemokine Receptor–Related Genetic Sequences in an African Green Monkey Simian Cytomegalovirus–Derived Stealth Virus; *Experimental and Molecular Pathology;* 2000; pp. 10–16.

Michelson, S., Interaction of Human Cytomegalovirus with Monocytes/Macrophages: A Love–Hate Relationship; *Path. Biol.;* 1997; pp. 146–158; vol. 45, No. 2.

Michaelson, Susan; Cytomegalovirus (CMV) and sequestration of chemokines; *Eur. Cytokine Netw.;* Jun. 1999; pp. 286–287; vol. 10, No. 2.

Michelson, Susan, et al.; Modulation of RANTES Production by Human Cytomegalovirus Infection of Fibroblasts; *Journal of Virology;* Sep. 1997; pp. 6495–6500; vol. 71, No. 9.

Monti, Gianpaola, et al.; Intrapulmonary Production of RANTES During Rejection and CMV Pneumonitis After Lung Transplantation; *Transplantation;* Jun. 27, 1996; pp. 1757–1762; vol. 61, No. 12.

Murayama, Tsugiya, et al.; Potential Involvement of IL–8 in the pathogenesis of human cytomegalovirus infection; *Journal of Leukocyte Biology;* Jul. 1998; pp. 62–67; vol. 64.

Neote, Kuldeep, et al. Molecular Cloning, Functional Expression, and Signaling Characteristics of a C–C Chemokine Receptor; *Cell;* Feb. 12, 1993; pp. 415–525; vol. 72.

Nishiyori, Atsushi, et al.; Localization of fractalkine and $CX_3CR1$ mRNAs in rat brain; does fractalkine play a role in signaling from neuron to microglia?; *FEBS Letters;* 1998; pp. 167–172; vol. 429.

Nordøy, Ingvild, et al.; Immunologic Parameters as Predictive Factors of Cytomegalovirus Disease in Renal Allograft Recipients; *The Journal of Infectious Diseases;* 1999; pp. 195–198; vol. 180.

Pass, Robert F., et al.; A Subunit Cytomegalovirus Vaccine Based on Recombinant Envelope Glycoprotein B. and a New Adjuvant; *The Journal of Infectious Diseases;* 1999; pp. 970–975; vol. 180.

Penfold, Mark E.T.; et al.; Cytomegalovirus encodes a potent α chemokine; *Proc. Natl. Acad. Sci. USA;* Aug. 1999; pp. 9839–9844; vol. 96.

Pleskoff, Olivier, et al; The Cytomegalovirus–Encoded Chemokine Receptor US28 Can Enhance Cell–Cell Fusion Mediated by Different Viral Proteins; *Journal of Virology;* Aug. 1998; pp. 6389–6397; vol. 72, No. 8.

Quinnan Jr., M.D., Gerald V., et al.; Comparative Virulence and Immunogenicity of the Towne Strain and a Nonattenuated Strain of Cytomegalovirus; *Annals of Internal Medicine;* 1984; pp. 478–483; vol. 101.

Rawlinson, William D., et al.; Analysis of the Complete DNA Sequence of Murine Cytomegalovirus; *Journal of Virology;* Dec. 1996; pp. 8833–8849; vol. 70, No. 10.

Reusch, Uwe, et al.; A cytomegalovirus glycoprotein re–routes MHC class I complexes to lysosomes for degradation; *EMBO Journal;* 1999; pp. 1081–1091; vol. 18, No. 4.

Reyburn, Hugh T., et al.; The Class I MHC homologue of Human Cytomegalovirus inhibits attack by natural killer cells; *Nature;* Apr. 3, 1997; pp. 514–517; Vol 386.

Rollins, Barrett J.; Chemokines; *Blood;* Aug. 1, 1997; pp. 909–928; vol. 90, No. 3.

Saederup, Noah, et al.; Cytomegalovirus–encoded β chemokine promotes monocyte–associated viremia in the host; *Proc. Natl. Acad. Sci. USA;* Sep. 1999; pp. 10881–10886; vol. 96.

Sallusto, Federica, et al.; Chemokines and chemokine receptors in T–cell priming and Th1/Th2–mediated responses; *Immunology Today;* Dec. 1998; pp. 568–574; vol. 19, No. 12.

Seow, Heng–Fong; Pathogen interactions with cytokines and host defence: an overview; *Veterinary Immunology and Immunopathology;* 1998; pp. 139–148; vol. 63.

Shellam, G.R.; The Potential of Murine Cytomegalovirus as a Viral Vector for Immunocontraception; *Reprod. Fertil. Dev.;* 1994; pp. 401–409; vol. 6.

Streblow, Daniel N., et al.; The Human Cytomegalovirus Chemokine Receptor US28 Mediates Vascular Smooth Muscle Cell Migration; *Cell;* Nov. 24, 1999; pp. 511–520; vol. 99.

Swiss–Prot Accession No. P16849; Aug. 1, 1990.

Thäle, Regine, et al.; Identification and Expression of an Murine Cytomegalovirus Early Gene Coding for an Fc Receptor;*Journal of Virology;* Dec. 1994; pp. 7757–7765; vol. 68, No. 12.

Tomasec, Peter, et al.; Surface Expression of HLA–E, and Inhibitor of Natural Killer Cells, Enhanced by Human Cytomegalovirus gpUL40; *Science;* Feb. 11, 2000; pp. 1031–1033; vol. 287.

Viera, Jeffrey, et al.; Functional Analysis of the Human Cytomegalovirus US28 Gene by Insertion Mutagenesis with the Green Fluorescent Protein Gene; *Journal of Virology;* Oct. 1998; pp. 8158–8165; vol. 72, No. 10.

Branch, Andrea D.; A good antisense molecule is hard to find; *TIBS 23;* Feb. 1998; pp. 45–50.

Crooke, Stanely T. et al.; *Antisense Research and Applications; Basic Principles of Antisense Therapeutics;* chapters 1–3; pp. 1–53.

Crystal, Ronald G.; Transfer of Genes to Humans: Early Lessons and Obstacles to Success; *Science;* pp. 404–410; Oct. 20, 1995; vol. 270.

Francken, Bart J.B., et al.; Human 5–Hydroxytryptamine$_{5A}$ Receptors Activate Coexpressed $G_i$ and $G_o$ Proteins in *Spodoptera frugiperda* 9 Cells; *Molecular Pharmacology;* pp. 1034–1044; May 2000; vol. 57, No. 5.

Ha, Hunjoo, et al.; Atherogenic lipoproteins enhance mesangial cell expression of platelet–derived growth factor: Role of protein tyrosine kinase and cyclic AMP–dependent protein kinase A; *J Lab Clin Med;* pp. 456–465; May 1998; vol. 131, No. 5.

Koyama, Noriyuki, et al.; Heparan Sulfate Proteoglycans Mediate a Potent Inhibitory Signal for Migration of Vascular Smooth Muscle Cells; *Circulation Research;* pp. 305–313; Aug. 10, 1998; vol. 83, No. 3.

Kung, H.F., et al.; Dopamine D–2 Receptor Imaging Radiopharmaceuticals: Synthesis, Radiolabeling, and in Vitro Binding of (R)–(+)–and (S)–(–)–3–Iodo–2–hydroxy–6–methoxy–N–[(1–ethyl–2–pyrrolidinyl) methyl] benzamide; *Journal of Medical Chemistry;* pp. 1039–1042; 1988; vol. 31, No. 5.

McNall, Steven J., et al.; Novel Serotonin Receptors in Fasciola. Characterization by Studies on Adenylate Cyclase Activation and [$^3$H]LSD Binding; *Biochemical Pharmacology;* pp. 2789–2797; 1984; vol. 33, No. 17.

Padia, J.K., et al; Design and Synthesis of Novel Nonpeptide CCK–B Receptor Antagonists; *Bioorganic & Medicinal Chemistry Letters;* pp. 805–810; 1997; vol. 7, No. 7.

Padia, J.K., et al.; Novel Nonpeptide CCK–B Antagonists: Design and Development of Quinazolinone Derivatives as Potent, Selective, and Orally Active CCK–B Antagonists; *Journal of Medicinal Chemistry;* pp. 1042–1049; 1998; vol. 41, No. 7.

Palù, Giorgio, et al.; In pursuit of new developments for gene therapy of human diseases; *Journal of Biotechnology;* pp. 1–13; 1999; vol. 68.

Schall, T.J., et al., Biology of the Rantes/SIS Cytokine Family; *Cytokine;* pp. 165–183; May 1991; vol. 3, No. 3.

Schofield, J.P., et al.; Non–viral approaches to gene therapy; *British Medical Bulletin;* pp. 56–71; 1995; vol. 51, No. 1.

Verma, Inder M., et al.; Gene therapy—promises, problems and prospects; *Nature;* pp. 239–242; Sep. 18, 1997; vol. 389.

Wang, T.S., et al.; A Simple Method of Preparation for [$^{123}$I]–(S)–(—)–IBZM; *Applied Radiation and Isotopes;* pp. 369–372; 1998; vol. 49, No. 4.

Hwang, Eung–Soo et al.; Induction of Neutralizing Antibody Against Human Cytomegalovirus (HCMV) with DNA–Mediated Immunization of HCMV Glycoprotein B in Mice; *Microbiol. Immunol.;* 1999; pp. 307–310; vol. 43, No. 3.

Krause, Philip R., et al.; Herpevirus Vaccines; Development, Controversies, and Applications; *New Vaccines and New Vaccine Technology;* Mar. 1999; pp. 61–61; vol. 13, No. 1.

Kravitz, Rachel H., et al.; Cloning and characterization of rhesus cytomegalovirus glycoprotein B; *Journal of General Virology;* 1997; pp. 2009–2013; vol. 78.

Kropff, Barbara, et al.; Identification of the gene coding for rhesus cytomegalovirus glycoprotein B and immunological analysis of the protein; *Jorunal of General Virology;* 1997; pp. 1999–2007.

* cited by examiner

| | | | | |
|---|---|---|---|---|
| 10 ATGAATAACA | 20 CATCTTGCAA | 30 CTTCAACGTC | 40 ACTCTCAACG | 50 CATCGGCACC |
| 60 AAGCCGATAC | 70 ATAGCTATTG | 80 CTATGTACAG | 90 CATTGTTATC | 100 TGTATCGGGT |
| 110 TGGTTGGAAA | 120 CCTGCTGTTA | 130 TGCATCGTGT | 140 TAGTCAAGAA | 150 ACGCAAACTG |
| 160 CGATATTCCA | 170 GCGATGTTTA | 180 TTTTTTCCAC | 190 GCCTCTATGG | 200 CCGACCTCGT |
| 210 CAGCACTGTC | 220 ATGCTACCGC | 230 TCTGGCTACA | 240 TTATGTCCTC | 250 AACTTTGCCC |
| 260 AACTCTCTCG | 270 AGGAGCCTGT | 280 ATCAGCTTTT | 290 CGGTGACTTT | 300 CTATGTTCCC |
| 310 CTTTTCGTTC | 320 AGGCCTGGTT | 330 ACTCATTTCC | 340 ATCGCTATGG | 350 AGCGATATTC |
| 360 CAACTTAGTA | 370 TGGATGGCAC | 380 CCATTAGCGT | 390 TAAGACGGCC | 400 TTTAAACACT |
| 410 GCATAGGAAC | 420 CTGGATCGTA | 430 TCTGCCTTCG | 440 TGGCATCACC | 450 CTACTACGCA |
| 460 TACAGAAACT | 470 CACACGACGA | 480 ACACGAATGC | 490 ATTCTAGGAA | 500 ACTACACTTG |
| 510 GCACATTAAC | 520 GAACCGCTAC | 530 ACACGTGTAT | 540 GGATGTGGTG | 550 ATCATAGTAT |
| 560 GGACCTTTTT | 570 GGCCCCAGTA | 580 CTGGTAACCA | 590 TTATAGCAAG | 600 CGTCAAAATG |
| 610 AGACGAACGA | 620 CCTGGGCAA | 630 TACTAGGTTA | 640 AACGAAAAGA | 650 ACAGCGACAT |
| 660 TCTTATAGTA | 670 CTAGTTGTCA | 680 TGACAGTGTT | 690 CTTTTGGGA | 700 CCGTTTAATA |
| 710 TCGTGTTGGT | 720 TATTGACAAT | 730 ATTTTACAGA | 740 GATACTATGA | 750 TACCACGAAT |
| 760 TGCGATGTAG | 770 AAAAGATTAA | 780 ACATATCATG | 790 GCTATGATCT | 800 CAGAAGCCAT |
| 810 TGTTTATTTT | 820 CGCGGTATTA | 830 CAGCACCTAT | 840 TATTTATGTA | 850 GGGATTAGTG |
| 860 GCAGATTTCG | 870 CGAAGAGATT | 880 TACTCTCTGT | 890 TTAGACGCCA | 900 GCCGTATAAC |
| 910 GATTTGGACC | 920 CCGATGCCAA | 930 TCAATTCATG | 940 ATTGAACTCA | 950 CTAGCCAGGG |
| 960 AAGAAGTAGA | 970 AATAGAAATG | 980 CTAGACAATC | 990 GGAAAGCAAT | 1000 GTACCGCAAC |
| 1010 CAGAAGAATG | 1020 CTTCTGGTAA | | | |

FIG. 1

```
        10         20         30         40         50
ATGACCAACG CCGGACACTG TCACATAAAC GAAAGTCTCG CGTCGTATGG
        60         70         80         90        100
AATCGCTCCC GCAGCTACCA TTACCTTATA CAGCATTGCG GGAATCTGCG
       110        120        130        140        150
GTGTCACGGG AAATCTGTTA ATACTTTTGG TTTTGTTCAC GAGACGCATA
       160        170        180        190        200
CACTGGTTCG CAAATGACAT CTACTATCTC AACATGATCT TTACAGACTT
       210        220        230        240        250
TCTTGTTTTC ATTACATTAC CCGCCTGGGT TTACTACCTG CTGAATTACA
       260        270        280        290        300
CACAACTCTC ACACTATGCC TGCATTGCTC TATCATTTGT TTTTTACGTT
       310        320        330        340        350
TCCATTTTTA TTCAAGCTGA CTTTATGGTA GCAGTGGCTA TCGAGCGTTA
       360        370        380        390        400
TCGAAGCCTA GTGAAAAACA AACCCCTTAG CGTAAAAAAA GCCAGCGTCA
       410        420        430        440        450
GCTGCGCGTG CATCTGGATC ATTGTTATTA TAGTGTCTTC ACCATACTAC
       460        470        480        490        500
ATGTTAGAT  CGCAACACGA AACAAATTCT TGCATTCTAG GAAACTACAC
       510        520        530        540        550
CTGGCATATG AACAGTCCTT TTCGCACCAC AATGGACGCA TCCATTAACA
       560        570        580        590        600
TTTGGTCTTT TGTCGTTCCG GCCGTGACGA CCTTGTTAAT AGCCAGACGA
       610        620        630        640        650
ATTTATGTAT GTACTTCAGG CAACAAAAAA ATGAACGCCA GAGCCAGTGG
       660        670        680        690        700
TTTGTTAGAG GCCATGGTGA TTAGCATGTT ATTCTTCGGA GGACTTTTCA
       710        720        730        740        750
ACCTGAACAT CTTTCGAGAC ATAGTTTCGG ACACATCGGA AGACAATAAA
       760        770        780        790        800
GACTGCACAT ATCTTAAGCA GGAACACTTT ATTCGCATGG TCGGTGTGGC
       810        820        830        840        850
CCTCGTTTAC GGGCGCGCTA TATTCAACCC TTTTATGTAT ATGTGTGTGA
       860        870        880        890        900
GTACCAGATT GCGCCAAGAA ATAAAATGTT TGTTTATGCG AATACCTTAT
       910        920        930        940        950
GAAACACTAG ATGCAGAACA CGCTAAACTC ATGGTTAATT TAAAAAACAG
       960        970        980        990       1000
AAATGCTAAT GTACCCGATC CTAAACCTCG TGAATATGAA TCTGTGTTAT
      1010
AG--------
```

FIG. 2

```
         10         20         30         40         50
    ATGACCAACA CTAACAATAC GACTTGTCAT CTCAACGGAA CTTTCGAAAC
         60         70         80         90        100
    TTTTAAAATC ACCCGTCCAG TAGCCATCAG CGCCTACACT GTACTCGTGG
        110        120        130        140        150
    TTATCGGACT TTTGGGAAAC ATTGTGCTGC TCAGCGTGCT CGTCGTGAAA
        160        170        180        190        200
    CGCAAGCTCA AGTTTCCGAA TGACATTTAC TTTTTCAACG CGTCTTTGGC
        210        220        230        240        250
    AGACGTTTTT GCCGTCTGCA TGTTGCCCGC CTGGGTTAAC TATGCACTGG
        260        270        280        290        300
    ACTCCACACA ACTTAGCAAG TTCTCATGTA TCACTTTTAC GTTTGGTTTT
        310        320        330        340        350
    TACGTCTCCC TGTTCATCCA GGCCTGGATG CTCATTCTGG TCACCCTGGA
        360        370        380        390        400
    GCGATACGGA TCTCTAGTCT GGATCGCCCC GATCACCAGA AACAAAGCCA
        410        420        430        440        450
    TAGCGAATTG TGTACTCTTT TGGCTTGTTT CCATCTTCTT GGCCGCACCT
        460        470        480        490        500
    TACTACTCTT TTAGAAACGA AAGCAACGAA CACCAATGCA TCATGAGAAA
        510        520        530        540        550
    CTATACCTGG AGCGTTGGTG AAACATGGCA CATAGCCCTG GATTTCTTAA
        560        570        580        590        600
    TTACGCTCAT TACATTTATC ATGCCAGTGA CTATTGTGTT AGCTCTGAGT
        610        620        630        640        650
    TTCAAAATGG CCAGATGGTC AACCTTTGGT TACAGAAACC TCACCAGCAG
        660        670        680        690        700
    AACCAGTCTT ATCCTTATTT TGATACTGAC AGTAGCAGCA GGGTTCTGGG
        710        720        730        740        750
    GACCTTTTCA CCTATTTATG TTTATAGAAA ACGTGGCAGG GCAGATTTAC
        760        770        780        790        800
    CACATTCAAA AGGATTGCTG GTACTTACAG CTCAGACACT TGTGTAGCTT
        810        820        830        840        850
    GATGACCGAA ACCCTAGTGT TTCTACGTTC AGTTTTTAAC CCTTATATTT
        860        870        880        890        900
    ATATGATAAT CAGTTACAAG TTTAGGCAGC AGGTGCGCAG TCTACTCAAG
        910        920        930        940        950
    CGTACTCAGT ATGATGCTTT GGACACGACT CAGTTAGCAG AAACTATGCA
        960        970        980        990       1000
    GCTGAAAGCG AAAGGTGTGC CGGTGTCCGA CCCCGCGCCG CATGACTGCG
       1010       1020
    AATGCTTTTT GTAA------

FIG. 3
```

|     |     |     |     |     |
| --- | --- | --- | --- | --- |
| 10  | 20  | 30  | 40  | 50  |
| ATGAATTCGA | GCCAGCACAA | CATAAGCGTG | TTTCTCTCCA | TTGGAGCAGG |
| 60  | 70  | 80  | 90  | 100 |
| GCCCGTCATT | ACCGGATACA | CGTGCGTTTT | TCTGTTCGGG | ATTCTGGGAC |
| 110 | 120 | 130 | 140 | 150 |
| ACTTTTACTT | GTATTGGAAA | AACCATCAGA | GACGACACCG | GACAAACAGT |
| 160 | 170 | 180 | 190 | 200 |
| TTCAGTGATG | TTTTATTTCG | ACATCTCATG | ATCACCGAAG | AGGTCTTTAC |
| 210 | 220 | 230 | 240 | 250 |
| CCTCACCATT | CCCGTCTGGG | CGTATCACTT | AACTACTCAC | GGCAACTTAC |
| 260 | 270 | 280 | 290 | 300 |
| CGGGCTCGTG | GTGCCGAAGT | CTCACCTTCG | TTTTTTATCT | AACGGTATTC |
| 310 | 320 | 330 | 340 | 350 |
| GCTCGTGCCT | TCTTTTACCT | GCTCCTCATC | TGGGACCGAT | ACAGCGTAAT |
| 360 | 370 | 380 | 390 | 400 |
| CATCTGCAGA | CACCCTCTCC | CCGTTAATCT | GAACTACAGT | CAGGTCATAG |
| 410 | 420 | 430 | 440 | 450 |
| GCCTGTCTGT | CTGGCTGGTT | GCCGTACTGT | CAGCATCACC | GTTCTCCATT |
| 460 | 470 | 480 | 490 | 500 |
| TTTAACGGAA | GTGTGAAACA | ATGCCTGGGC | AACATGGGCA | GCATACCCAG |
| 510 | 520 | 530 | 540 | 550 |
| CGAATCGTCT | GCCGTTCTTA | ACCTGGAAGT | GCACCTGTGC | TCCTTCTGGT |
| 560 | 570 | 580 | 590 | 600 |
| TACCGCTCAT | CATGTCGGCT | AACTGTTACT | ACCAAGCAAA | ACGCCGAGCA |
| 610 | 620 | 630 | 640 | 650 |
| TCGCCTGACC | AACTCCACGA | ACTTTACCGA | TGCAGTTTGC | TAATTACCATA |
| 660 | 670 | 680 | 690 | 700 |
| TTCACAACT | TACGCTATCG | TATGGTTTCC | TTTCCATCTC | GCTTTACTCA |
| 710 | 720 | 730 | 740 | 750 |
| TAGACGCCCT | GATTAGCATA | AGCCATGTAG | AACCCTCTAG | CGCTCTCCAC |
| 760 | 770 | 780 | 790 | 800 |
| TGGGCATCCA | TTGTCGTTAC | CTGTAAATCA | TTTACATTTG | TATATGCGGG |
| 810 | 820 | 830 | 840 | 850 |
| CATAAGCCCA | CTAGTGTATT | TCACATGCTG | CCCCACCGTA | CGTCGCGAAC |
| 860 | 870 | 880 | 890 | 900 |
| TGCTGATGTC | TCTACGTCCA | TTCTTCACCT | GGATTTCCAG | CAAAACGCGG |
| 910 | 920 | 930 | 940 | 950 |
| CGAGGCTACG | CTCCGATTAA | AACACAACCT | TTAAACATCC | CCGACGAGCC |
| 960 | 970 | 980 | 990 |     |
| GATAGATAAC | AAGTCACCGC | ACCTGTTAAA | CGAATAA--- |     |

FIG. 4

|  |  |  |  |  |
|---|---|---|---|---|
| 10 | 20 | 30 | 40 | 50 |
| ATGACTACCA | CCACAATGAG | TGCTACCACG | AATTCCAGTA | CCACGCCTCA |
| 60 | 70 | 80 | 90 | 100 |
| AGCAAGCAGC | ACCACGATGA | CAACGAAGAC | AAGCACTCCT | GGCAATACAA |
| 110 | 120 | 130 | 140 | 150 |
| CTACTGGCAC | TACGTCCACC | CTGACAACGA | TATCAACAAC | TTCTAATGCT |
| 160 | 170 | 180 | 190 | 200 |
| ACCAGCATAA | CGTCTAATTT | AAGCACTACC | GGAAACCAAA | CTGCAACTAC |
| 210 | 220 | 230 | 240 | 250 |
| CAATGCTACT | ACCTTCAGTT | CCACATTAAC | AACATCTACA | AATATAAGCA |
| 260 | 270 | 280 | 290 | 300 |
| GTACATTTTC | GACAGTTTCT | ACCGTCGCAT | CCAATGCAAC | ATGTAATTCT |
| 310 | 320 | 330 | 340 | 350 |
| ACAATCACAA | CGAATATTAC | AACTGCTTTT | ACTACAGCAG | CAAACACTAC |
| 360 | 370 | 380 | 390 | 400 |
| CGCAAGCAGC | CTCACCAGCA | TCGTAACTTC | ACTTGCCACT | ACCATTGAAA |
| 410 | 420 | 430 | 440 | 450 |
| CCACATCATT | TGATTATGAT | GAGTCAGCAG | AAGCTTGCAA | CTTAACAGAC |
| 460 | 470 | 480 | 490 | 500 |
| ATCGTTCATA | CTACTAGATC | AGTGACAGTT | ACTTTCTATA | CTATCATATT |
| 510 | 520 | 530 | 540 | 550 |
| CATACTCGGC | CTTTTGGGAA | ACTTTCTGGT | TCTTATGACC | ATCATTTGGA |
| 560 | 570 | 580 | 590 | 600 |
| ACCGTCGCAT | TTCCTTTATG | GTTGAAATAT | ATTTCGTTAA | TCTAGCAATC |
| 610 | 620 | 630 | 640 | 650 |
| TCCGATCTTA | TGTTTGTATG | TACTTTACCA | TTTTGGATAA | TGTATCTTCT |
| 660 | 670 | 680 | 690 | 700 |
| TGAGCACGAC | GTCATGTCAC | ATGCATCCTG | TGTAGCAATG | ACAGCCATTT |
| 710 | 720 | 730 | 740 | 750 |
| TTTATTGCGC | GCTGTTTGCC | AGCACTGTTT | TCCTCTTGCT | AATTGTTTTA |
| 760 | 770 | 780 | 790 | 800 |
| GACAGATGTT | ACGCTATTCT | ATTAGGTACA | GAAAAAGCAA | ATAGACGTTT |
| 810 | 820 | 830 | 840 | 850 |
| ATTGCGCAAT | GCTGTTTCTG | GATGCATGCT | CATGTGGGGA | TTGTGTTTCA |
| 860 | 870 | 880 | 890 | 900 |
| TTTTAGCATT | ACCTCATTTT | ATCTTTATGA | AGAAAGGAAC | CAACGTATGT |
| 910 | 920 | 930 | 940 | 950 |
| GTAGCAGAGT | ATGAACCAGG | ACTTAACAAT | TTCTATGTTA | TTTTTATCAA |
| 960 | 970 | 980 | 990 | 1000 |
| TACTGAGGTG | AACCTATGCA | CCCTAGTTTT | GCCAGCCGCA | GCCATTATCT |

FIG. 5A

|      1010  |      1020  |      1030  |      1040  |      1050  |
|------------|------------|------------|------------|------------|
| ACTGGTATCT | TAAACTAACC | AAAGCACTCA | AAACCCATGA | ACGACTGCGT |
|      1060  |      1070  |      1080  |      1090  |      1100  |
| CATAGGCTAA | CGTCTCTAAA | CATAGTGTTA | GCTGTTGTCA | TTGTATTTGC |
|      1110  |      1120  |      1130  |      1140  |      1150  |
| TTTGTTTTGG | CTGCCGTATA | ATCTCATGCT | TATGATGTAT | AGCTTAGTTC |
|      1160  |      1170  |      1180  |      1190  |      1200  |
| ACATGCAGAT | ACCTTGGGAA | TGCAGCTCTG | AAAAAATACT | GAGACGAAGT |
|      1210  |      1220  |      1230  |      1240  |      1250  |
| TTAATTATTA | CAGAATCCAT | CGCCCTCAGT | CACTGTTGCA | TCAACCCCAT |
|      1260  |      1270  |      1280  |      1290  |      1300  |
| TATCTACTTG | CTCTTCGGAC | CTCGCTGTCG | AAGCGAGTTC | TGTCACCTGT |
|      1310  |      1320  |      1330  |      1340  |      1350  |
| TGCGATGTTG | CTTTACGCGC | TTATGTCCAC | ACAGATCCTG | GAGTTCCATA |
|      1360  |      1370  |      1380  |      1390  |      1400  |
| CGTGCAGAGA | CGGTGTCCAT | CAGTCTCAGT | CACTCACAGG | TATCTGCATC |
|      1410  |      1420  |      1430  |      1440  |      1450  |
| ATCTGAGGAT | GATGACAACG | ATGTGCATGA | TGAATTGCAA | TTTTTAATTT |
|      1460  |            |            |            |            |
| GA         |            |            |            |            |

FIG. 5B

|  |  |  |  |  |
|---|---|---|---|---|
| 10 ATGACCAATC | 20 TTTACTCTGC | 30 CAATTTTCTC | 40 ACCTTGATAG | 50 TACTTCCTTT |
| 60 TATCGTTTTA | 70 AGCAATCAAC | 80 ACCTTTTACC | 90 TGCCAGTGCA | 100 GTAACCTGTA |
| 110 AATTTCTCTC | 120 CCTGTTGTAC | 130 TACTCTAGCT | 140 GCAGCGTAGG | 150 TTTTGCTACA |
| 160 GTGGCACTGA | 170 TAGCGGCCGA | 180 CCGATACCGA | 190 GTGATTCATC | 200 GCCGAACTCA |
| 210 AGCTCGCCAA | 220 TCCTACCGTA | 230 ACACATATAT | 240 GATAGTAGGC | 250 TTAACGTGGC |
| 260 TCATTGGCTT | 270 GATCTGCGCT | 280 ACCCCGGGG | 290 GGGTCTACAC | 300 AACCATTGTA |
| 310 GCTCACCGCG | 320 ATGGGGAAAG | 330 TGATGCTCAA | 340 AGACACAATA | 350 CTTGCATTAT |
| 360 GCACTTTGCG | 370 TATGATGAAG | 380 TTTACGTCCT | 390 CATGGTCTGG | 400 AAACTTCTCA |
| 410 TCGTTTTAGT | 420 CTGGGGCATA | 430 GTGCCAGTTG | 440 TCATGATGAG | 450 CTGGTTTTAC |
| 460 GCGTTTTTTT | 470 ACAATACTGT | 480 ACAAAGAACA | 490 GCCAAAAAAC | 500 AACAACGTAC |
| 510 GTTGAAATTC | 520 GTAAAGGTAT | 530 TACTCCTGTC | 540 ATTCATCATC | 550 ATCCAAACTC |
| 560 CCTATGTGTC | 570 AATCATGATT | 580 TTTAACACGT | 590 ATGCCACCGT | 600 AGGATGGCCG |
| 610 ATGGAATGCG | 620 CCGATCTAAC | 630 TAGACGCCGA | 640 GTCATCAACA | 650 CGTTTTCCCG |
| 660 TCTCGTCCCC | 670 AATCTACATT | 680 GCATGGTCAA | 690 CCCCATCCTC | 700 TACGCTCTCA |
| 710 TGGGAAATGA | 720 CTTTGTGTCT | 730 AAAGTGGGCC | 740 AATGCTTTCG | 750 GGGGAACTC |
| 760 ACGAACCGTC | 770 GAACTTTTCT | 780 GCGTTCCAAG | 790 CAACAAGCCC | 800 GCAACTCGGA |
| 810 CGATGTACCG | 820 ACAATTGTCA | 830 GTCAACAACC | 840 CGCCACACCC | 850 ACCATCGTCA |
| 860 ATAAGCCCGA | 870 AAAAAACCCG | 880 CACGTAAAAC | 890 GCGGTGTATC | 900 TTTCAGCGTC |
| 910 AGCGCATCTT | 920 CCGAACTCGC | 930 AGCGGCCAAA | 940 AAAGCCAAAG | 950 ACAAAGCCAA |
| 960 GCGGCTTTCC | 970 ATGTCCCACC | 980 AAAACCTACG | 990 TCTGACGTGA |  |

FIG. 6

|     |     |     |     |     |
|---|---|---|---|---|
| 10<br>ATGGCAGTCA | 20<br>CTTTACGAGG | 30<br>CGGCAGCCCG | 40<br>ATAAACTTTA | 50<br>AACTCATGAT |
| 60<br>TGTCAGCCAC | 70<br>AGAAACCGGA | 80<br>AATTTCACGA | 90<br>GATACGGCTG | 100<br>TTTCAGCGTT |
| 110<br>CTGCTATCCG | 120<br>TCCAGGCGGG | 130<br>TTATGGAAAC | 140<br>CATTCTTCAC | 150<br>AACCGAACG- |
| 160<br>---------- | 170<br>---------- | 180<br>---------- | 190<br>---------- | 200<br>---------- |
| 210<br>---------- | 220<br>---------- | 230<br>---- AGTGA | 240<br>AACTAATTCC | 250<br>ATTTTGCACA |
| 260<br>TCAACACCAC | 270<br>CTGCAATGTG | 280<br>ACCGACTCAC | 290<br>TGTACGCCGC | 300<br>CAAACTAGGC |
| 310<br>GAAGCCCTCG | 320<br>TGAACAGCGC | 330<br>GCTAGCTTTA | 340<br>TTCGGTACCC | 350<br>CCCTCAACGC |
| 360<br>CATCGTCCTC | 370<br>GTCACACAGC | 380<br>TATTGGCCAA | 390<br>CCGAGTTCAT | 400<br>GGATACTCCA |
| 410<br>CCCCGATTAT | 420<br>CTACATGACC | 430<br>AATCTTTACT | 440<br>CTGCCAATTT | 450<br>TCTCACCTTG |
| 460<br>ATAGTACTTC | 470<br>CTTTTATCGT | 480<br>TTTAAGCAAT | 490<br>CAACACCTTT | 500<br>TACCTGCCAG |
| 510<br>TGCAGTAACC | 520<br>TGTAAATTTC | 530<br>TCTCCCTGTT | 540<br>GTACTACTCT | 550<br>AGCTGCAGCG |
| 560<br>TAGGTTTTGC | 570<br>TACAGTGGCA | 580<br>CTGATAGCGG | 590<br>CCGACCGATA | 600<br>CCGAGTGATT |
| 610<br>CATCGCCGAA | 620<br>CTCAAGCTCG | 630<br>CCAATCCTAC | 640<br>CGTAACACAT | 650<br>ATATGATAGT |
| 660<br>AGGCTTAACG | 670<br>TGGCTCATTG | 680<br>GCTTGATCTG | 690<br>CGCTACCCCC | 700<br>GGGGGGGTCT |
| 710<br>ACACAACCAT | 720<br>TGTAGCTCAC | 730<br>CGCGATGGGG | 740<br>AAAGTGATGC | 750<br>TCAAAGACAC |
| 760<br>AATACTTGCA | 770<br>TTATGCACTT | 780<br>TGCGTATGAT | 790<br>GAAGTTTACG | 800<br>TCCTCATGGT |
| 810<br>CTGGAAACTT | 820<br>CTCATCGTTT | 830<br>TAGTCTGGGG | 840<br>CATAGTGCCA | 850<br>GTTGTCATGA |
| 860<br>TGAGCTGGTT | 870<br>TTACGCGTTT | 880<br>TTTTACAATA | 890<br>CTGTACAAAG | 900<br>AACAGCCAAA |
| 910<br>AAACAACAAC | 920<br>GTACGTTGAA | 930<br>ATTCGTAAAG | 940<br>GTATTACTCC | 950<br>TGTCATTCAT |
| 960<br>CATCATCCAA | 970<br>ACTCCCTATG | 980<br>TGTCAATCAT | 990<br>GATTTTAAC | 1000<br>ACGTATGCCA |

FIG. 7A

|      1010  |      1020  |      1030  |      1040  |      1050  |
|------------|------------|------------|------------|------------|
| CCGTAGGATG | GCCGATGGAA | TGCGCCGATC | TAACTAGACG | CCGAGTCATC |
|      1060  |      1070  |      1080  |      1090  |      1100  |
| AACACGTTTT | CCCGTCTCGT | CCCCAATCTA | CATTGCATGG | TCAACCCCAT |
|      1110  |      1120  |      1130  |      1140  |      1150  |
| CCTCTACGCT | CTCATGGGAA | ATGACTTTGT | GTCTAAAGTG | GGCCAATGCT |
|      1160  |      1170  |      1180  |      1190  |      1200  |
| TTCGGGGGA  | ACTCACGAAC | CGTCGAACTT | TTCTGCGTTC | CAAGCAACAA |
|      1210  |      1220  |      1230  |      1240  |      1250  |
| GCCCGCAACT | CGGACGATGT | ACCGACAATT | GTCAGTCAAC | AACCCGCCAC |
|      1260  |      1270  |      1280  |      1290  |      1300  |
| ACCCACCATC | GTCAATAAGC | CCGAAAAAAA | CCCGCACGTA | AAACGCGGTG |
|      1310  |      1320  |      1330  |      1340  |      1350  |
| TATCTTTCAG | CGTCAGCGCA | TCTTCCGAAC | TCGCAGCGGC | CAAAAAAGCC |
|      1360  |      1370  |      1380  |      1390  |      1400  |
| AAAGACAAAG | CCAAGCGGCT | TTCCATGTCC | CACCAAAACC | TACGTCTGAC |
|      1410  |            |            |            |            |
| GTGA------ |            |            |            |            |

FIG. 7B

|  |  |  |  |  |
|---|---|---|---|---|
| 10 | 20 | 30 | 40 | 50 |
| ATGATTACGG | AGCGCGTCCT | CGCAGGCATC | CTCGCGGGCA | TGACGGCCGC |
| 60 | 70 | 80 | 90 | 100 |
| GGGGAGTTTG | GTCATTCTCC | TCGCGGTTGT | TATGTGGTTG | AACATGTTAG |
| 110 | 120 | 130 | 140 | 150 |
| ATCGCGCTGG | CATGCCAATG | GCCGTTGGGC | ATTACACAGG | GAACCTGGTG |
| 160 | 170 | 180 | 190 | 200 |
| TTGACTCAGG | TCATCTGTAT | CTTCTCCATG | CTGGCGTCTA | AAATTGTTGG |
| 210 | 220 | 230 | 240 | 250 |
| CATGACGAGT | GCGGCCAACA | TGGGCTTCTG | CGGCATCGTG | GTTTTCTGG |
| 260 | 270 | 280 | 290 | 300 |
| AAGACACTGG | CCTCTATGTC | ACCTCGCTGC | TCTTCATGTT | TATGATCCTG |
| 310 | 320 | 330 | 340 | 350 |
| GATCGCATGG | CGGCTTTTCT | TAACGGGCGT | CTTTTCTGGA | GGCAGCAGAC |
| 360 | 370 | 380 | 390 | 400 |
| GACGAAGCAG | AATCTGAGTA | CAAGCGTGTA | CATTATTCTG | TTTTGCTGGG |
| 410 | 420 | 430 | 440 | 450 |
| TGTTGGGAAT | GGCCGCGGCT | GTTCCCAGCG | CGGCTGTGGC | TGCACCCAAT |
| 460 | 470 | 480 | 490 | 500 |
| TCCAGGTGGG | AACGCTGCGA | AATTCCAGTG | TCATATGCCG | CAATCGACAT |
| 510 | 520 | 530 | 540 | 550 |
| GATTGTGAAG | CTCTGGTTTG | TGCTGTTGGC | ACCCGTCGTG | CTGATTATGG |
| 560 | 570 | 580 | 590 | 600 |
| CTGTGATCAT | TCAATCTTCC | TATCATCGTG | ATCGGGAGAG | GATCTGGTAC |
| 610 | 620 | 630 | 640 | 650 |
| TATGCCAGAC | GTGTGTTCAT | GTTCTACACG | GCCTGCTTTG | TCATGATGGT |
| 660 | 670 | 680 | 690 | 700 |
| GCCTTATTAC | TTCGTCAGAG | TCATGCTGAG | CGACTTTGCT | TTGGTTGATA |
| 710 | 720 | 730 | 740 | 750 |
| TAAAAACAAA | AACGGCGAAC | AGCGACGGTT | GTGATTCGAC | ATTTCTTGAT |

FIG. 8A

|     |     |     |     |     |
| --- | --- | --- | --- | --- |
| 760 | 770 | 780 | 790 | 800 |
| TATCTGAACA | TGTTCACTCA | CGTGATTTAC | AGTTTTAAGT | TGGTGGTGTT |
| 810 | 820 | 830 | 840 | 850 |
| TGCTTTGTTC | ATTGTCCTGT | TTTGCTCCAT | AAACCCGATG | GAAACGCTGG |
| 860 | 870 | 880 | 890 | 900 |
| AAGAATGCTT | GGAGAGGGCC | GATGCTGAGA | GGCAAAGTCG | GTCAGAAGCA |
| 910 | 920 | 930 | 940 | 950 |
| TCCCAGGGTG | AAAGGAGGCT | GCCAATCAAC | ACATGCTGTA | TAAAGTTGAT |
| 960 | 970 | 980 | 990 | 1000 |
| TGAATTGATA | AAGCAGTATG | TAAGCACTCT | CTCTAAAGCC | ACGAGGGACA |
| 1010 | 1020 | 1030 | 1040 | 1050 |
| ATTCTGGCGA | AAGGGCCAAT | TTGCCAGAGA | ATGCTGAAGA | TATTGGAACA |
| 1060 | 1070 | 1080 | 1090 | 1100 |
| ACTGGCAGTG | ATCAGCTACC | GACTGAGGTC | ACCGTGACCC | CAAATTCATC |
| 1110 | 1120 | 1130 | 1140 |     |
| GGCTGTGTTT | AGCACTGGAG | GAACGGTGTC | TCCAGTCTAA |     |

METHODS AND COMPOSITIONS USEFUL FOR STIMULATING AN IMMUNE RESPONSE

CROSS-REFERENCE TO RELATED APPLICATIONS

This application claims the benefit of U.S. Provisional Application No. 60/265,925, filed Feb. 2, 2001, which is incorporated herein by reference in its entirety for all purposes.

STATEMENT AS TO RIGHTS TO INVENTIONS MADE UNDER FEDERALLY SPONSORED RESEARCH AND DEVELOPMENT

This invention was partially made with government support under Grant Number N66001-01-C-8009 awarded by the Defense Advanced Research Projects Agency (DARPA) of the Department of Defense. The government may have certain rights in this invention.

BACKGROUND

Cytomegaloviruses (CMVs) are common pathogens and are members of the β subgroup of the herpesvirus family. CMV is a slow replicating, species-specific complex DNA virus found in most mammals. CMV has adopted subtle evolutionary strategies for evading the immune system of an infected host, while disseminating through the host tissues.

The genome (230 kb) of human CMV (HCMV) includes a long and short unique region (UL and US, respectively), each of which is flanked by inverted repetitions. The entire HCMV genome has been sequenced (Chee, M. S., et al. (1990) *Curr. Top. Microbiol. Immunol.* 154:125–169) and appears to contain over 200 open reading frames.

One of these open reading frames is referred to as US28, which encodes a protein (also "US28") that acts as a functional receptor for certain human and viral chemokines (see, e.g., Gao & Murphy, 1994, *J Biol Chem.* 269:28539–42). Upon infection of a cell by CMV, US28 is expressed on the surface of the infected cell and becomes capable of responding to chemokines in the environment. Three other open reading frames called US27, UL33 and UL78 encode for proteins having homology to US28 as shown in Table 1 below.

TABLE 1

Exemplary Viral Chemokine Elements

| CMV Chemokine Elements | GenBank Accession No. | Reference |
|---|---|---|
| US27 | X17403 | Chee et al, 1990, Nature, 344:774 |
| US28 | L20501, AF073831-35 | Neote et al, 1993, Cell, 72:415-25 |
| UL33 | X53293 | Chee et al, 1990, Nature, 344:774 |
| UL78 | X17403 | Chee et al, 1990, Nature, 344:774 |

Chemokine receptors such as US28 generally are G protein coupled receptors. Structurally these receptors have seven transmembrane segments that loop in and out of the cell membrane, as well as an intracellular tail that is coupled to a G protein signal transducing molecular complex.

The chemokines themselves constitute a subgroup of a larger class of signaling proteins and have the ability, among other things, to promote cellular migration (Zlotnik et al. (1999) *Crit. Rev. Immunol.* 19:1–47). The chemokines generally are divided into four groups based upon the arrangement of certain cysteine residues within the protein that can form disulfide bonds. One class of chemokines is the beta chemokines that are characterized by having two adjacent cysteines; this structure is referred to in shorthand form simply as CC. The beta chemokines are involved in attraction of monocytes and leukocytes. The alpha chemokines, in contrast, have a single amino acid separating the two cysteine residues, and thus their structure is designated as CXC. These chemokines are primarily involved in attracting polymorphonuclear cells. The fractalkines or delta-chemokines constitute a third class of chemokines and tend to be cell bound molecules. The two cysteines in this class are separated by three amino acid residues, a structure designated as CX3C. This class of chemokines are expressed at high levels in the brain; some evidence indicates that the fractalkines are involved in neuron-glial cell interactions (see, e.g., Harrison, et al. (1998) *Proc. Natl. Acad. Sci. U.S.A.* 95:10896–10901; and Nishiyori, A. et al. (1998) *FEBS Lett.* 429:167–172). The US28 receptor of HCMV is characterized in part by its very strong affinity for fractalkine. The structure of the final class of chemokines is simply referred to as C (also gamma-chemokines), because these chemokines contain only a single N-terminal cysteine involved in a disulfide bond. The chemokine receptors have varying specificity for the different classes of chemokines. Some chemokine receptors can bind chemokines from different classes.

BRIEF DESCRIPTION OF THE FIGURES

FIG. 1 shows the polynucleotide sequence of the rhUS28.1 coding sequence (SEQ ID NO:1).

FIG. 2 shows the polynucleotide sequence of the rhUS28.2 coding sequence (SEQ ID NO:2).

FIG. 3 shows the polynucleotide sequence of the rhUS28.3 coding sequence (SEQ ID NO:3).

FIG. 4 shows the polynucleotide sequence of the rhUS28.4 coding sequence (SEQ ID NO:4).

FIGS. 5A–5B show the polynucleotide sequence of the rhUS28.5 coding sequence (SEQ ID NO:5).

FIG. 6 shows the polynucleotide sequence of the rhUL33 coding sequence (SEQ ID NO:6).

FIGS. 7A–7B show the polynucleotide sequence of the rhUL33 spliced coding sequence (SEQ ID NO:7).

FIG. 8 shows the polynucleotide sequence of the rhUL78 coding sequence (SEQ ID NO:8).

SUMMARY

Compositions containing recombinant or modified cytomegalovirus (CMV) are provided herein, as well as methods utilizing such compositions to generate an immune response and/or in various therapeutic or prophylactic treatments. Some of the recombinant CMV contain a targeting sequence that targets the recombinant CMV to the immune system cells and tissues of the host in which the composition is to be administered. Typically, the targeting sequence is a heterologous chemokine element, such as a chemokine or chemokine receptor. Other recombinant CMV incorporate a heterologous sequence that encodes for an immunogenic protein or peptide; such modified CMV can serve as a vehicle for delivering a selected antigen to a host to generate a desired immune response. Certain other modified CMV are attenuated by disabling a viral dissemination gene to reduce the virulency of the modified CMV in the host. Still other recombinant CMV incorporate some or all of the foregoing elements.

Thus, certain recombinant cytomegalovirus (CMV) comprise a cytomegalovirus (CMV) genome which comprises a first heterologous nucleotide sequence encoding a heterologous chemokine element (i.e., a targeting sequence), and (ii) a second heterologous nucleotide sequence encoding an immunogenic polypeptide. The recombinant CMV is typically encapsulated to form an infectious and biologically active virus. The heterologous chemokine element is generally selected to be endogenous to the host in which the composition is to be administered, as this facilitates targeting of the recombinant CMV to the immune tissues of the host. As indicated supra, the heterologous chemokine element can 5 be a chemokine or chemokine receptor. Specific examples of such elements useful when the host is a mammal include, but are not limited to, MIP3a, SLC, MDC, MC10, MIP1β, ELC and CCR7, or homolog thereof.

The heterologous nucleotide sequence that encodes the immunogenic polypeptide is typically a sequence that encodes an antigen from a pathogenic organism or for a tumor antigen, but this is not required. The pathogenic organism can be a bacterium, virus, or parasite, for example.

Some of these recombinant CMV are further modified such that the CMV is attenuated to reduce virulency in a host. As noted supra, the CMV genome can be attenuated in various ways, such as disabling a viral dissemination gene. Such genes can be those that encode a viral chemokine element or a viral immune-modulatory gene. The viral chemokine elements can be a chemokine, chemokine receptor or a soluble chemokine binding protein, for example. Specific examples of such chemokines and chemokine receptors include, for example, US28, US27, UL33, UL78, UL146, UL147, MCK-1 and MCK-2, or a homolog thereof. The viral immune-modulatory genes are those viral genes that modulate the anti-viral immune response of an infected host so as to facilitate viral infection. Specific examples of such genes include, but are not limited to, UL111A, US3, US6, US11, US2, UL83, UL18, UL40, m144, m152, m04, m06, and m138, or a homolog thereof.

The foregoing recombinant CMV can optionally be formulated as a composition. Such compositions then contain recombinant CMV and a pharmaceutically acceptable adjuvant, carrier, diluent or excipient.

Recombinant CMV such as just described can be utilized in methods to induce an immune response in a host. In general such methods involve administering a composition to a host, wherein the composition comprises a recombinant cytomegalovirus (CMV) with a genome that contains (i) a first heterologous nucleotide sequence encoding a heterologous chemokine element, and (ii) a second heterologous nucleotide sequence encoding an immunogenic polypeptide. The heterologous chemokine element and immunogenic polypeptide are as just described for the recombinant CMV compositions and reagents. The recombinant CMV may also be attenuated by disabling one or more viral dissemination genes as described supra. In some instances, the nucleotide sequence that encodes the immunogenic polypeptide is selected to encode an antigen correlated with a disease or infection which the host has or is susceptible to obtaining. Such is the case for therapeutic and prophylactic treatment methods which are discussed below. However, the sequence need not encode for such an antigen. This is sometimes the case when a study is performed with an animal model (e.g., rhesus monkey or mice). For instance, a study may be under taken in rhesus monkeys or mice to make a preliminary assessment of the effectiveness of a recombinant CMV encoding for an antigen that appears to be correlated with a human disease.

As just alluded to, the recombinant CMV that are provided are also useful in treatment methods, either therapeutically or prophylactically. Some of these methods involve administering a composition to an animal, wherein the composition comprises an attenuated recombinant cytomegalovirus (CMV) with a genome that contains (i) a first nucleotide sequence encoding a chemokine receptor or chemokine that is endogenous to the animal, and (ii) a second nucleotide sequence encoding an immunogenic polypeptide. Because the immunogenic polypeptide comprises an antigen correlated with a disease or infection which the animal has or is susceptible to obtaining, and the administered composition induces an immune response in the animal, the method provides effective therapeutic or prophylactic treatment.

DETAILED DESCRIPTION

I. Definitions

As used in this specification and the appended claims, the singular forms "a," "an" and "the" include plural references unless the content clearly dictates otherwise.

Unless defined otherwise, all technical and scientific terms used herein have the meaning commonly understood by a person skilled in the art to which this invention belongs. The following references provide one of skill with a general definition of many of the terms used in this invention: Singleton et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger et al. (eds.), Springer Verlag (1991); and Hale & Marham, THE HARPER COLLINS DICTIONARY OF BIOLOGY (1991).

The following definitions are provided to assist the reader in the practice of the invention.

As used herein, the term "cytomegalovirus (CMV)" has the normal meaning in the art and refers to one of a family of double stranded DNA viruses of the betaherpes group with positional and genomic similarity to human herpes virus 5 (cytomegalovirus) including, without limitation, human CMV AD169 (ATCC #VR 538), human CMV Towne (ATCC #VR 977), human CMV Davis (ATCC #VR 807), human CMV Toledo (Quinnan et al, 1984, *Ann Intern Med* 101: 478–83), monkey CMV Rh68.1 (ATCC #VR 677), monkey CMV CSG (ATCC #VR 706), rat CMV Priscott (ATCC #VR 991), mouse CMV Smith (ATCC #VR 1399) and others. "ATCC" is the American Type Culture Collection, 10801 University Boulevard, Manassas, Va. 20110–2209, USA. The 230-kb dsDNA genome of human and murine CMV were sequenced (see, e.g., Chee et al., 1990, *Curr. Top. Microbiol. Immunol.* 154:125–169; also see Rawlinson, 1996, *J Virol.* 70:8833–49, both incorporated herein in their entirety).

Various open reading frames from human CMV (HCMV) are referred to herein using the nomenclature of Chee et al [e.g., US28, US33, US78 (human US28, human US33, human US78, respectively)]. In general, reference to such reading frames from HCMV also refer to the sequences of sequence and positional homologs of such reading frames found in different HCMV strains, including sequences in any naturally occurring HCMV strain, and mutations to such strains. In some instances the term can also refer to various splice variants not yet characterized in the literature. With respect to the protein, the protein encoded by the HCMV reading frame refers to the protein having a native amino acid sequence, as well as variants and fragments regardless of origin or mode of preparation.

As used herein the term homolog has its usual meaning in the art. The term generally refers to a nucleic acid or protein that has substantial sequence identity with respect to a reference sequence and, in the case of a protein, typically shares at least one activity with the reference sequence. Thus, for example, the term "US28 homolog" refers to a nucleic acid or protein that has sequence homology with US28 and at least one activity of US28, typically the ability to bind a chemokine, especially fractalkine. The US28 homolog can be from CMV native to various animals, including various mammals (e.g., human and non-human primates, specifically monkeys, chimpanzee, gorilla and baboon). Thus, US28 homologs can include, but are not limited to, human US27, human UL33, and human UL78. Additional homologs from rhesus monkey (macaca mulatta) CMV can include rhUS28.1, rhUS28.2, rhUS28.3, rhUS28.4, rhUS28.5, rhUL33 and rhUL78.

As used herein, the term "immunogen" has the normal meaning in the art and refers to a molecule that can elicit an adaptive immune response upon injection or delivery by another mode into a person or animal, typically a peptide, polypeptide, glycoprotein, lipopolysaccharide or glycosaminoglycan. An "immunogenic polypeptide" is a polypeptide that is an immunogen.

As used herein, the term "antigen" has the normal meaning in the art and refers to a molecule that reacts with antibodies or elicits an immune response.

As used herein, the term "antigen presenting cell (APC)" has the normal meaning in the art and refers to a cell that can present antigen in the context of MHC I or MHC II to efficiently stimulate immune effector or helper cells (e.g., dendritic cells and macrophages).

As used herein, the term "resident dendritic cell (RDC)" has the normal meaning in the art and refers to a subclass of dendritic cells that, in the unstimulated state, are resident in peripheral tissue or organs rather than migratory. An exemplary RDC is a Langerhan cell, which is resident in skin.

As used herein, the term "secondary lymphoid organs" has the normal meaning in the art. Secondary lymphoid organs include lymph nodes, spleen and mucosal-associated lymphoid tissues such as tonsils and Peyer's patches.

As used herein, the term "chemokine element" refers to a chemokine or chemokine receptor or other (e.g., soluble) chemokine binding protein.

As used herein, the terms "chemokine" and "chemokine receptor" have their normal meanings in the art. Chemokines are a class of cytokines that play an important role in inflammatory responses, leukocyte trafficking, angiogenesis, and other biological processes related to the migration and activation of cells. As mediators of chemotaxis and inflammation, chemokines play roles in pathological conditions. As described in the Background section, known chemokines are typically assigned to one of four subfamilies based on the arrangement of cysteine motifs and include: the alpha-chemokines, the beta-chemokines, the gamma chemokines and the delta- chemokines. For a recent review on chemokines, see Ward et al., 1998, *Immunity* 9:1–11 and Baggiolini et al., 1998, *Nature* 392:565–568, and the references cited therein. Chemokine activity may be mediated by chemokine receptors. For example, several seven-transmembrane-domain G protein-coupled receptors for C—C chemokines have been cloned: a C—C chemokine receptor-1 which recognizes MIP-1α, RANTES, MCP-2, MCP-3, and MIP-5 (Neote et al., 1993, *Cell,* 72:415–415); CCR2 which is a receptor for MCP1, 2, 3 and 4 or 5; CCR3 which is a receptor for RANTES, MCP-2, 3, 4, MIP-5 and eotaxin; CCR5 which is a receptor for MIP-1α, MIP-1β and RANTES; CCR4 which is a receptor for CMDC or TARC; CCR6 which is a receptor for LARC; and CCR7 which is a receptor for SLC and MIP-3° (reviewed in Sallusto et al., 1998, *Immunol. Today* 19:568 and Ward et al., 1998, *Immunity* 9:1–11).

The terms "nucleic acid" "polynucleotide" and "oligonucleotide" are used interchangeably herein and refer to a deoxyribonucleotide or ribonucleotide polymer in either single- or double-stranded form, and unless otherwise limited, encompasses known analogues of natural nucleotides that hybridize to nucleic acids in a manner similar to naturally-occurring nucleotides. Unless otherwise indicated, a particular nucleic acid sequence includes the complementary sequence thereof A "subsequence" or "segment" refers to a sequence of nucleotides that comprise a part of a longer sequence of nucleotides.

A "primer" is a single-stranded polynucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically is at least 7 nucleotides long and, more typically range from 10 to 30 nucleotides in length. Other primers can be somewhat longer such as 30 to 50 nucleotides long. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target DNA to which a primer hybridizes.

As used herein, a "recombinant expression cassette" or simply an "expression cassette" is a nucleic acid construct, generated recombinantly or synthetically, that has control elements that are capable of affecting expression of a gene that is operably linked to the control elements in hosts compatible with such sequences. Expression cassettes typically include at least promoters and optionally, transcription termination signals and polyadenylation signals. Typically, the recombinant expression cassette includes at least a nucleic acid to be transcribed (e.g., a nucleic acid encoding a non-viral chemokine or antigenic peptide sequence) and a promoter. Additional factors necessary or helpful in effecting expression can also be used as described herein. For example, transcription termination signals, enhancers, and other nucleic acid sequences that influence gene expression, can also be included in an expression cassette.

As used herein, the term "host" refers to an animal, e.g., a mammal such as a rodent, mouse, monkey, human or non-human primate, model animals, or agriculturally important livestock such as bovines, porcines, poultry, that can be infected by naturally occurring CMV or recombinant CMV as described herein.

As used herein, an "immune response" has the ordinary meaning in the art and, unless otherwise specified, refers to an adaptive immune response to a specific antigen. In one aspect, an immune response involves the concerted action of lymphocytes, antigen presenting cells, phagocytic cells, and various soluble macromolecules in defending the body against infection, cancer or other exposure to non-self molecules. The immune response can be detected and quantified (e.g., following immunization) by measuring cellular or humoral responses according to numerous assays known in the art (see, e.g., Coligan et al., 1991 (suppl. 1999), CURRENT PROTOCOLS IN IMMUNOLOGY, John Wiley & Sons (hereinafter, sometimes "Coligan")). For example, to detect a cellular immune response, T cell effector effects against cells expressing the antigen are detected using standard assays, e.g., target-cell killing, lymphocyte proliferation, macrophage activation, B-cell activation or lymphokine production. Humoral responses are measured by detecting the appearance of, or increase in titer of, antigen-specific antibodies using routine methods such as ELISA. The progress of the antibody response can be determined by measuring class switching (i.e., the switch from an early IgM response to a later IgG response.

As used herein, "viral dissemination" has the normal meaning in the art, and refers to a detectable increase in viral titer or amount at sites other than the primary infection (inoculation) site, e.g., by transmission of virus from sites of primary infection or reactivation to secondary sites (e.g., tissues or organs). Virus dissemination typically involves transmission of virus from sites of primary infection (e.g., mucosal tissues such as oral or genital mucosal endothelia) or reactivation (e.g., blood leukocytes including myeloid progenitor cells in the bone marrow and peripheral blood monocytes) to secondary sites (e.g., tissues or organs including salivary glands, kidney, spleen, liver and lungs) where viral replication and amplification may occur. Without intending to be bound by a particular mechanism, dissemination may involve assisted movement of virus from primary sites (e.g., by random or directed migration of infected cells), release of virus into the bloodstream and random or directed attachment of this virus to cells at secondary sites, or other modes.

As used herein, the term "substantial sequence identity," refers to two or more sequences or subsequences that have at least 60%, preferably 80%, most preferably 90%, 95%, 98%, or 99% nucleotide or amino acid residue identity, when compared and aligned for maximum correspondence, as measured using one of the following sequence comparison algorithms or by visual inspection. "Moderate sequence identity" refers to two or more sequences or subsequences that have at least 25% sequence identity, sometimes at least 28% or 30% sequence identity. Sequence identity that is less than substantial sequence identity can be significant, i.e., can be indicative of homology between molecules when other factors the (e.g., conserved motifs, functional similarity or structural similarity) are present, or, in the case of proteins, when a number of non-identical residues are similar (i.e., conserved). Two sequences (amino acid or nucleotide) can be compared over their full-length (e.g., the length of the shorter of the two, if they are of substantially different lengths) or over a subsequence such as at least about 50, about 100, about 200, about 500 or about 1000 contiguous nucleotides or at least about 10, about 20, about 30, about 50 or about 100 contiguous amino acid residues. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Natl. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). Each of these references and algorithms is incorporated by reference herein in its entirety. When using any of the aforementioned algorithms, the default parameters for "Window" length, gap penalty, etc., are used. One example of algorithm that is suitable for determining percent sequence identity and sequence similarity is the BLAST algorithm, which is described in Altschul et al., 1990, *J Mol. Biol.* 215:403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff & Henikoff, 1989, *Proc. Natl. Acad. Sci. USA* 89:10915) alignments (B) of 50, expectation (E) of 10, M=5, N=−4, and a comparison of both strands.

As used herein, the term "immune-inhibitory protein" or "immune modulatory protein" refers to CMV-encoded proteins that are believed to suppress or otherwise modify a host immune response to viral infection. An "immune-inhibitory gene" or "an immune modulatory gene" are genes that encode such proteins.

As used herein, an "endogenous" gene, polynucleotide, or polypeptide sequence is a gene, polynucleotide, or polypeptide sequence naturally occurring in a specified organism. For example, for CMV, an endogenous chemokine gene is a chemokine encoded by a wildtype CMV. Conversely, an "exogenous" sequence is one not naturally occurring in a specified organism. For example, for CMV, an gene sequence encoding a human chemokine is an exogenous sequence.

A "heterologous sequence" or a "heterologous nucleic acid," or a "heterologous polypeptide sequence" as used herein, is one that originates from a source foreign to the particular host cell or genome. Thus, in a virus genome, a synthetic or mammalian (e.g., rodent, Murine, bovine, porcine, human, non-human primate) gene sequence (e.g., such as a gene encoding a mammalian chemokine or chemokine receptor) is heterologous.

An "immunogenic amount" of a compound, agent or composition is an amount sufficient to induce an immune response in a host animal when administered to the host.

As used herein in the context of a gene sequence (e.g., in a CMV genome), the term "disabled" refers to a gene that is mutated, deleted or partially deleted in a coding or regulatory (e.g., promoter) sequence, such that the gene product (e.g., protein or RNA) that is encoded by the gene is not expressed or is not expressed in biologically active form.

As used herein, the term "peptide" refers to short (e.g., less than about 25-residues) polypeptides. Peptides are typically at least 6 residues in length, often at least 7 or eight residues. The term "polypeptide" refers polymers of amino acids and is includes peptides. In some embodiments, polypeptides are from about at least 6, 8, 10, or at least 25 residues up to about 100, 200, 500, 1000 or 2000 residues, e.g., between about 6 and about 500 residues, often between about 6 and about 200 or about 6 and about 100 residues. In some embodiments, polypeptides are from about 25 to about 100, about 25 to about 200, or about 25 to about 500 residues in length.

II. Introduction

Novel methods and reagents useful for inducing an immune response in a host to which the reagents are administered are provided herein. These reagents and methods include and utilize cytomegalovirus (CMV) that is genetically engineered to effectively deliver antigens (viral or exogenous) to immune system cells and tissues in the host (e.g., by altering the trafficking of cells that are infected with the genetically engineered virus and/or by altering the antigenic or immunogenetic potential of the virus).

In general this is accomplished by modifying the viral genome such that: (1) CMV is attenuated (i.e., rendered less pathogenic than wild type virus), typically by mutating (e.g., deleting) a gene that affects viral dissemination; and/or (2) the viral genome expresses a specified or predetermined antigenic or immunogenic polypeptide sequence to which an immune response is desired; and/or (3) the viral genome expresses a targeting element (e.g., a heterologous chemokine element such as a chemokine receptor or ligand) that effectively targets the virus to host immune system cells and tissues (e.g., professional antigen presenting cells or secondary lymphoid organs), resulting in an accelerated and/or more potent immune response against the antigen compared to conventional vaccination methods. It is contemplated that one, two or more of these changes are introduced.

The CMV that is modified can be a wild-type strain, a clinical strain, an attenuated strain, and/or a genetically engineered strain (e.g., comprising mutations other than those specifically introduced to accomplish the mutations described herein). Furthermore, the recombinant CMV disclosed herein is not limited to human CMV (HCMV). Similar recombinant CMV can be obtained for essentially any strain that infects animals, including humans, non-human primates and various commercial livestock. Specific examples of such modified CMV include rhesus monkey CMV (rhCMV) and murine CMV (mCMV) that incorporate the modifications disclosed herein.

The recombinant CMV can exist as a naked polynucleotide, but in the methods disclosed herein is generally encapsulated to form an infectious and biologically active virus. Furthermore, the recombinant CMV provided need not include the entire genome. As already indicated, certain genes can be deleted to attenuate the virus. Other genes can also be deleted or modified, provided the resulting virus is still capable of infecting the desired host or replicating and/or disseminating to the degree necessary to elicit an immune response.

Attenuation of the modified CMV is typically achieved by disabling one or more viral "dissemination genes." A dissemination gene is generally a gene that encodes a chemokine element (e.g., a chemokine receptor, chemokine or chemokine binding protein) or a gene that plays a role in immune-modulation in the host. The nucleotide sequence encoding the immunogenic polypeptide is selected to encode at least an antigen to which one wants to raise antibodies. Typically, the antigen is one expressed by a pathogenic organism (e.g., a virus, a bacterium or a parasite) or a tumor antigen. The targeting element is generally a chemokine element that is endogenous to the host to facilitate delivery of the virus to the desired immune tissues or secondary lymphoid organs in the host. Often the chemokine element is a chemokine receptor or ligand that is expressed in the host.

Certain recombinant CMV provided herein include all three of the foregoing modifications and alter the activity of the virus in two ways. First, inclusion of a nucleotide sequence that encodes for an immunogenic protein (or fragment or variant thereof) results in expression of an immunogen which elicits an immune response in the host. Second, attenuation of the virus and modification of the CMV genome to include a nucleotide targeting segment collectively function to alter the dissemination pattern of the virus. As indicated supra, in certain embodiments CMV is attenuated to reduce virulency in the host by disabling a viral gene that functions in viral dissemination such that the encoded viral protein is not expressed in active form. Without intending to be bound by a particular mechanism, this modification impairs 'wild-type' CMV dissemination (which favors the virus establishing latent infection and may enhance pathogenicity). While the resulting virus is attenuated, it nonetheless serves as a vector for delivery of the encoded immunogenic polypeptide in the host. Engineering CMV to express a targeting element such as at least one non-viral (heterologous) chemokine element acts to target the virus to immune system tissues and cells in the host animal. This results in a change in the viral dissemination pattern from that of wild-type virus, which favors the virus establishing a latent infection, to a pattern that favors dissemination to specified host immune system cells and tissues. These changes result in decreased viral pathogenesis (as a consequence of inhibition of the wild-type dissemination pattern) and increased immune response to the antigen (as a consequence of dissemination of the virus to host lymphoid cells capable of initiating an immune response). In some instances, the modified CMV is as just described but is not attenuated. Such modified CMV finds utility in certain applications for targeting a specific immunogen to lymphoid tissue in a host.

Other modified CMV provided herein include one or two of the three modifications listed above. Thus, for instance, certain modified CMV are engineered to include just the sequence that encodes for an immunogenic polypeptide; optionally, such modified CMV is also attenuated. Such modified CMV can be utilized to generate an immune response in the host. Other modified CMV are engineered to encode for a targeting element such as a chemokine receptor or ligand, and optionally are also attenuated as discussed above. Such modified virus is useful for targeting CMV bearing additional heterologous elements to specific immune tissues in a host.

In still other instances, the viral genome is modified to encode at least one non-viral (heterologous) chemokine element, and optionally at least one viral dissemination gene normally present in the wild-type virus is disabled, but the immunogen is a viral protein (i.e., expressed by wild-type CMV). Compositions containing such modified viruses are used to stimulate an adaptive immune response to CMV itself. In an embodiment, the viral genome is engineered to over-express the immunogenic viral polypeptide, or to express an immunogenic variant of the viral polypeptide.

The modified CMV compositions that are provided can be utilized to generate an immune response in a variety of hosts including humans and non-humans, including, for example, non-human primates such as rhesus monkeys and other mammals such as mice and rats. The generation of such immune responses can be utilized in diverse therapeutic and prophylactic treatment methods by facilitating the generation of antibodies against a particular antigen associated with a disease or infection, for example. Methods performed with non-humans can serve as models for human responses.

The following sections provide further details regarding certain aspects of the compositions and methods that are provided, as well as specific examples of such compositions and methods.

3. CMV Chemokine Element and Immune-Modulatory Genes

3.1 Viral Dissemination and Dissemination Genes

Cytomegaloviruses disseminate (move from the site of infection or latency to other sites in the host) following infection or reactivation. Although free virus particles (virions) can disseminate, dissemination is more often cell-mediated. That is, following infection of a cell by the virus, viral proteins are expressed by the cell and may be secreted or displayed on the cell surface. The expression of these viral proteins affects trafficking of the infected cells. Evidence indicates that dissemination of wild-type CMV is facilitated by several virus-encoded genes. Viral genes that encode proteins that function to promote viral dissemination are called "viral dissemination genes." In certain modified CMV provided herein, the pathogenic potential of CMV is attenuated by modification (e.g., disabling) of one or more CMV dissemination genes, thereby increasing the efficacy of the virus for delivery of immunogen to host immune system cells and tissues by decreasing pathogenicity.

Two classes of genes play important roles in viral dissemination; in certain of the modified CMV, the virus is attenuated by disabling genes from one or both of these classes. The first class of viral dissemination genes is a class of genes encoding "chemokine elements," i.e., chemokines and chemokine receptors or soluble chemokine binding proteins. As noted supra, chemokines are proteins that mediate cell migration and targeting. Virally-encoded chemokine elements facilitate viral dissemination by mechanisms that include, without limitation, affecting the movement and targeting of virally-infected cells (e.g., cells secreting and/or displaying viral chemokines and/or chemokine receptors) and calling uninfected cells to sites of viral infection (by virtue of chemokine elements displayed on virus particles or displayed on or secreted by infected cells). Exemplary CMV chemokine element genes that can be disabled to produce the viral preparations of the invention include, without limitation, viral genes encoded at the human CMV US27, US28, UL33, UL78, UL146, and UL147 loci, and homologs thereof in non-human CMV. Specific examples of such homologs of HCMV US28 in rhesus monkey include rhCMV US28.1, US28.2, US28.3, US28.4, and US28.5 (SEQ ID NOS. 1–5, respectively; see also FIGS. 1–5B). Additional rhesus homologs are rhUL33 (SEQ ID NO:6; see FIG. 6) and rhUL78 (SEQ ID NO:8; see FIG. 8) (homologs of HCMV UL33 and UL78, respectively), and rhUL33 spliced (SEQ ID NO:7; see FIGS. 7A–B), a splice variant of rhUL33. Additional chemokine element genes in murine CMV for which there are no known homologs in HCMV include mCK-1 and mCK-2.

The second class of viral dissemination genes are genes encoding immune-modulatory proteins, proteins that modulate the anti-viral immune response of an infected host to facilitate viral infection by, for example, (1) causing down-regulation of host MHC Class I (classical) and/or MHC Class II proteins, (2) inhibiting host cell production of cytokines (e.g., stimulatory cytokines IFN-α, IFN-γ, TNF-α, GM-CSF or IL-1α) by cells, e.g., PHA stimulated PBMC and LPS stimulated monocytes, (3) inhibition of cell proliferation (e.g., inhibit Con A/PHA induced proliferation of human and rhesus PBMC), and/or (4) enhancing surface expression of non-classical MHC I on monocytes (modulating protection from natural killer cell activity). Exemplary CMV immune-modulatory genes that can be disabled to produce the viral preparations include, without limitation, viral genes encoded at the HCMV UL111A, US3, US6, US11, US2, UL83, UL18, and UL40 loci, including homologs in other cytomegalovirus strains, e.g., other human CMV clinical strains or non-human strains, such as strains that infect monkeys or mice. As described in greater detail infra, homologs to each of the foregoing immune-modulatory sequences have been identified by the present inventors in rhesus monkeys with the exception of UL18 and can be utilized in the preparation of the current compositions and in the provided methods.

It will be recognized that the specification of exemplary chemokine element and immune-modulatory genes herein is not intended to be limiting. Other viral chemokine element and immune-modulatory genes, e.g., derived from other clinical strains of CMV or from non-human sources, may differ slightly in sequence or may be identified or discovered in the future. As will be appreciated by those of skill, such genes can be identified by DNA sequencing and cloning (e.g., by amplification using primers based on known sequences).

Various viral genes are described in additional detail in, e.g., §§3.2 and 3.3, and Table 2.

3.2. Viral CMV Chemokine Elements

As noted, viral chemokine elements refer to viral encoded proteins that are chemokines or chemokine receptors. Viral chemokines are identified by structural similarity (e.g., sequence similarity) to known chemokines (e.g., alpha, beta, gamma or delta chemokines) and biological activities characteristic of chemokines (e.g., chemotactic properties and induction of calcium mobilization activity). Viral chemokine receptors are identified by structural similarity (e.g., sequence similarity) to known chemokine receptors (e.g., seven-transmembrane-domain G protein-coupled receptors) and/or functional tests for chemokine binding, receptor-mediated signal transduction, and imparting chemokine dependent migratory activity on expressing cells. Exemplary viral (CMV) chemokine elements are described below. These viral chemokine elements are homologs of human chemokine receptors involved in cell chemotaxis and targeting.

3.2.1 CMV US28: The CMV genome contains an open reading frame designated US28, which encodes a protein that acts as a functional receptor for certain human and viral chemokines (see, e.g., Gao & Murphy, 1994, *J Biol Chem.* 269:28539–42). The sequence of US28 from HCMV strain VHL/E is found as Genbank accession no. L20501. US 28 sequences from the Toledo strain and AU4.1 strain of HCMV are the same and can be found as Genbank accession no. AF073831. It will be understood by those of skill that other US28 molecules, e.g., derived from other clinical strains of CMV, may differ slightly in sequence (see, e.g., Genbank accession nos. AF 073831–35; see also M. S. Chee, et al., 1990, Curr. Top. Microbiol. Immunol. 154:125–69), but are also useful in the preparations and methods disclosed herein.

As indicated above, a number of molecules with homology to US28 from HCMV have been identified in rhesus CMV. These homologs are referred to as rhUS28.1, rhUS28.2, rhUS28.3, rhUS28.4 and rhUS28.5. The polynucleotide sequences for these homologs are shown in FIGS. 1–5B and listed as SEQ ID NOS:1–5. There are several factors indicating that these sequences are homologs of human US28. First, the rhUS28 homologs show a relatively high level of similarity with human US28. In particular, there is significant similarity in hydrophobicity/ hydrophilicity alignments. The various rhUS28 genes also have hydrophobic and hydrophilic regions consistent with the class of seven member G proteins of which human US28 is a member. Additionally, the rhUS28 family of genes has positional homology with human US28. Given such similarity with human US28, disabling one or more of these genes can be a useful way for attenuating rhCMV preparations provided herein.

Further details regarding the rhUS28 homologs are provided in PCT Application No. 01/27392.

The US28 protein has a high level of sequence similarity to human G protein coupled receptors (Davis-Poynterand Farrell, 1996, *Immunol Cell Biol.* 74:513–22). Upon infection of a cell by CMV, US28 is expressed on the surface of the infected cell and becomes capable of responding to chemokines in the environment. Certain of the inventors have also found that US28 is expressed on virions. US28 has been shown to bind a variety of human, murine, and virus-encoded CC chemokines (Kledal et al., 1997, *Science* 277:1656–9; Kuhn et al., 1995, *Biochem Biophys Res Commun.* 211:325–30). In addition, the CX3C chemokine, fractalkine, binds with a very high affinity ($K_f$~50 pM) to US28 (Kledal et al., 1998, *FEBS Lett.* 441:209–14). Fractalkine is expressed on certain endothelial cell surfaces and on populations of dendritic cells (DC), and may thus define a portal through which CMV infected cells or virions go from the circulation to the tissue space, as well as find residence in the DC. US28 has been shown to bind and induce calcium mobilization through RANTES, MCP-1 and MIP1α in vitro, induce migration of smooth muscle cells to these ligands following transient or viral expression in vitro, and has been localized to cell and virion membranes.

3.2.2 CMV US27: CMV US27 is a US28 homolog, believed to be the result of a gene duplication event of US28 in HCMV (see, e.g., Chee et al, 1990, *Nature,* 344:774).

3.2.3 CMV UL146 (vCXC1): CMV UL146 encodes a CXC (alpha) chemokine homolog found in human CMV strains. Certain of the inventors have also demonstrated that a UL146 homolog exists in rhesus CMV. vCXC1 shows high inter-strain variability in amino acid sequence, but has conserved structural features, including the ELRCXC (SEQ ID NO:10) motif conserved in all clinical strains sequence to date. The protein encoded by the Toledo strain UL146 has been demonstrated to have neutrophil chemo-attractant properties and acts through the CXCR2 receptor (Penfold et al., 1999, *Proc Natl Acad Sci USA* 96:9839–44). Thus, the vCXC1 polypeptide appears to play a role in neutrophil-mediated dissemination of CMV.

3.2.4 CMV UL147 (vCXC2): UL147 (vCXC2), is a CXC (alpha) chemokine homolog in clinical and low passage strains of HCMV (Cha et al, 1996, *J Virology* 70: 78–83). Certain of the inventors have discovered that a UL147 homolog is present in rhesus CMV. This ORF shows high inter-strain variability in N terminal amino acid sequence, but has conserved structural features in all clinical strains sequenced to date. The UL147 gene product can induce weak calcium mobilization in THP-1 cells in response to recombinant vCXC2. vCXC2 is expressed as an early protein in infected cells in vitro.

3.2.5 CMV UL33: UL33 is a highly conserved G protein coupled receptor and is found in human, mouse and rat CMVs (Davis-Poynter et al., 1997, *J Virol.* 71:1521–9), and rhesus macaque CMV (see FIG. 6 and SEQ ID NO:6), as well as human herpes virus 6 (Gompels et al., 1995, *Virology* 209:29–51) & human herpes virus 7. The HHV6 homolog (U12) is reported to be a functional receptor for beta chemokines (Isegawa et al., 1998, *J Virol.* 72:6104–12).

Both rat and murine CMV UL33 have been shown to be dispensable for growth in culture but deletion of this ORF leads to decreased virulence in vivo (Beisser et al., 1998, *J Virol.* 72:2352–63; Davis-Poynter, supra). Human CMV UL33 has also been localized the envelope of infectious virions (Margulies et al., 1996, *Virology* 225:111–25).

Certain of the inventors have also identified a splice variant of UL33 in rhesus monkeys (see FIGS. 7A and B and SEQ ID NO:7). This particular splice variant can be described with reference to the nucleotide sequence set forth in SEQ ID NO:9 which is a segment that extends roughly 1000 nucleotides upstream of the rhUL33 reading frame and roughly a couple hundred nucleotides downstream. Assigning the first nucleotide of this sequence as nucleotide 1, with this particular splice variant, translation is initiated at nucleotide 603 through nucleotide 752, exon 1. An intron spanning nucleotide 753 to 830 is removed and exon 1 is joined to exon 2, nucleotide 831 to 2006. In contrast the unspliced gene runs through nucleotide 1017 to 2006 in this sequence. Thus, disabling the foregoing regions involved in the splice variant can also be utilized in the preparation of the compositions herein and in the present methods. Those of skill can identify other such splice variants using programs designed to identify splice variants such as the "Genefinder", "Genehunt" or "GRAIL" programs available at the CMS Molecular Biology resource found at www.unl.edu.

3.2.6 CMV UL78: Like UL33, homologs are present in murine (Rawlinson et al., 1996, *J Virol.* 70:8833–49), rat (Beisser et al., 1999, *J Virol.* 73:7218–30) and rhesus macaque (see FIG. 8 and SEQ ID NO:8) CMVs. Homologs exist in human herpes virus 6 & 7 (Gompels, 1995, supra). UL78 appear to encode a G protein coupled receptor, based on the structural characteristics such as trans-membrane spanning regions.

3.2.7 MCK-1, MCK-2: Murine CMV encodes two related CC chemokines (MCK-1 and MCK-2) encoded by alternate splicing of the m131/129 locus. The MCK-1 protein induce $Ca^{+2}$ flux in murine leukocytes in vitro (Saederup et al, 1999, *Proc. Nat. Acad. Sci. USA* 96:10881–86). Knockout of the m131/129 locus affects dissemination to the salivary gland, viral clearance from the spleen and liver and aspects of virally induced inflammation in mice in vivo (Fleming et al, 1999).

3.3 Viral Immune-modulatory Genes

As used herein, viral immune-modulatory genes are viral genes that encode proteins that exhibit immune suppressive or other immune modulatory activity, e.g., down-regulation of host MHC molecules, inhibition of host cell production of cytokines and/or inhibition of T cell proliferation. Exemplary viral (CMV) immune inhibitory genes are described below. Although the following information primarily focuses on genes from HCMV, it is anticipated that homologs to these genes exist in other mammalian CMVs, such as rhesus and murine CMV. In fact, certain of the inventors have identified homologs to all of the following genes from HCMV with the exception of UL18. Such sequences can be identified using various existing methods. For example, homologous sequences can be identified by DNA sequencing, cloning (e.g., by amplification using primers based upon known sequences), hybridization under stringent conditions using known sequences for immune-modulatory genes and by analyzing sequences with sequence comparison algorithms (e.g., BLASTN).

3.3.1 CMV UL111A: The CMV UL111A open reading frame encodes an IL-10-like polypeptide, see, e.g., Lockridge et al., 2000, *Virology* 268:272–80 (Rhesus CMV) and Kotenko et al., 2000, *Proc Natl Acad Sci USA* 97:1695–700 (human CMV). The CMV IL-10 homolog exhibits immune-modulatory activity (e.g., inhibition of production of stimulatory cytokines, inhibition of T lymphocyte proliferation; down-regulation of MHC Class I and II on monocytes. See, e.g., PCT Application No. 01/221831 for additional details concerning rhCMV UL111A.

3.3.2 CMV US3: US3 encodes an endoplasmic reticulum glycoprotein that prevents intracellular transport of MHC Class I molecules, thus inhibiting MHC class I mediated antigen presentation. See U.S. Pat. No. 6,033,671. Murine CMV encodes a homolog protein m152 (Ziegler H et al, Immunity. 1997 January 6(1):57–66).

3.3.3 CMV US6: US6 encodes an endoplasmic reticulum glycoprotein that prevents intracellular transport of MHC Class I molecules, thus inhibiting MHC class I mediated antigen presentation. See U.S. Pat. No. 6,033,671.

3.3.4 CMV US11: US11 encodes an endoglycosidase H-sensitive glycoprotein which inhibits surface expression of MHC Class I heavy chains. See U.S. Pat. No. 5,846,806.

3.3.5 US2: The US2 gene product induces export of MHC class I heavy chains from the endoplasmic reticulum via Sec61 (see, e.g., US Pat. No. 6,033,671).

3.3.6 UL83: The US2 gene product inhibits presentation of the 72kDa immediate early antigen to CD8+T cells (Gilbert et al., 1996, *Nature* 383:720–22).

3.3.7 UL18: UL18 is a viral homolog of the MHC class I molecule which inhibits lysis by natural killer cells by expressing on the infected cell surface ( Reyburn et al, 1997, *Nature,* 386: 514–17). Murine CMV encodes a homolog protein m144 (Farrell H E et al, *Nature.* 1997 April 3;386 (6624):510–4).

3.3.8 UL40: The N terminal fragment of UL40 induces surface expression of HLA-E on infected cells, hence protecting from natural killer cell mediated lysis (Tomasec et al, 2000, *Science,* 287:1031.)

3.3.9 m06: The murine CMV gene product m06 is resident in the endoplasmic reticulum, but upon binding to MHC I molecules is transported to lysosomes, hence facilitating destructruction of bound MHC I molecules Reusch U et al, EMBO J. 1999 February 15;18(4):1081–91).

3.3.10 m04: The murine CMV gene product m06 is resident in the endoplasmic reticulum, but upon binding to MHC I molecules is transported to the cell surface. It is believed its interaction with surface MHC I inhibits recognition by T cells or NK cells (Kleijnen et al, EMBO J. 1997 February 17;16(4):685–94).

3.3.11 m138: The murine CMV gene product m138 is a homolog of the murine Fc receptor glycoprotein and is able to interfere with humoral immunity to MCMV infected cells (Thale et al, J Virol. 1994 December 68(12):7757–65).

TABLE 2

Exemplary Viral Chemokine Elements and Immune-Modulatory Genes

| CMV Chemokine Elements or Immune-modulatory Genes | GenBank Accession No. | Reference |
|---|---|---|
| US27 | X17403 | Chee et al, 1990, Nature, 344:774 |
| US28 | L20501, AF073831–35 | Neote et al, 1993, Cell, 72:415–25 |
| UL33 | X53293 | Chee et al, 1990, Nature, 344:774 |
| UL78 | X17403 | |
| UL146 | U33331 | Cha et al, 1996, J.Virol, 70:78–83 |
| UL147 | U33331 | Cha et al, 1996, J.Virol, 70:78–83 |
| UL111A | AF202536 | Lockridge et al, 2000, Virology, 268:272–80 |
| US11 | X17403 | U.S. Pat. No. 5,846,806 |
| US3 | X17403 | U.S. Pat. No. 6,033,671 |
| US6 | X17403 | U.S. Pat. No. 6,033,671 |
| US2 | X17403 | U.S. Pat. No. 6,033,671 |
| UL83 | Xl 7403 | Gilbert et al. 1996 Nature 383, 720–722 |
| UL18 | X17403 | Reyburn et al, 1997 Nature, 386:514–517 |
| UL40 | X17403 | Tomasec et al, 2000, Science, 287:1031 |

3.4 Disabling CMV Dissemination Genes

Viral dissemination genes can be disabled in any of a variety of ways known in the art to produce the preparations of the invention, including: insertional mutagenesis in the promoter or protein-coding region, or partial or complete deletion of the target gene. In one embodiment, as described infra, the CMV target gene is disabled by insertion of a heterologous sequence encoding a human chemokine element. In designing primers, probes, and cloning strategy, useful CMV gene sequences are found in the scientific literature, including GenBank, or can be determined by routine methods based on known sequences. Methods for deletion and other forms of mutagenesis are well known, see, e.g., Ausubel at Chapter 8.

Heterologous Chemokine Elements 4.1 Generally

Certain of the modified CMV provided herein have incorporated in the CMV genome a heterologous nucleotide sequence encoding a heterologous (e.g., exogenous) chemokine element. As noted supra, the term "chemokine element" refers to chemokines, chemokine receptors and chemokine binding proteins. Without intending to be limited by any mechanism, the expression of the inserted heterologous chemokine element, as discussed infra, results in motility of the cells infected with the modified virus and particularly, dissemination of the cells to host immune cells and tissues. Preferred heterologous chemokine elements are those that mediate migration of cells in which they are normally expressed to immune system cells and tissues (e.g., secondary lymphoid organs) or, conversely, mediate migration of immune system cells (e.g., APCs) toward the cells or tissues that normally express the chemokine element. Useful heterologous chemokine elements include those identified as chemoattractant immune system cells (e.g., dendritic cells, or immature dendritic cells but not chemoattractant for one or more of mature dendritic cells, neutrophils, T-lymphocytes, monocytes, eosinophils). Such elements include those described in, or identified using the methods described in PCT Publication WO 01/80887.

Exemplary chemokine elements used in the practice of the invention are described, infra (§§4.1.1–4.1.5, and Table 3). Additional chemokine elements that may be used are known, see, e.g., the R&D Systems Catalog (1999) and (2000) R&D Systems Inc., 614 McKinley Place N.E. Min. 55413, the R&D online catalog at www.mdsystems.com (e.g., Jan. 1, 2001), the CYTOKINE FACTS BOOK, 1994, Academic Press Ltd., the CHEMOKINE FACTS BOOK, 1997, Academic Press Ltd., all incorporated by reference, and the GenBank protein sequence database http://www.ncbi.nlm.nih.gov/entrez/query.fcgi).

Typically, when the compositions of the invention are used for inducing an immune response in an animal, the chemokine element is selected to be from the same species as the host contemplated for the vaccine. For example, for a vaccine intended for use in human subjects, a human chemokine element is inserted into a virus able to infect human cells. Similarly, if a vaccine is intended for use in Rhesus monkeys, then a Rhesus chemokine element is inserted into a virus able to infect Rhesus cells. However, certain chemokine elements have cross-species activity and so it is not a requirement that the chemokine be from the same species as the host. While the following sections discuss primarily human chemokine elements, corresponding homologs are expected to be found in other mammals (e.g., monkeys and mice). As described supra in §3.2, such homologs can be identified by sequence similarity and biological activity similarity to known chemokine elements (e.g., chemokines or chemokine receptors).

Exemplary chemokine elements include, without limitation, the following:

4.1.1 CC chemokine receptor-7 (CCR7): CCR7 (EBI1) is a CC chemokine receptor belonging to a subfamily of G protein coupled receptors. CCR7 is most closely related to CCR9 and CCR6. CCR7 is expressed on mature dendritic cells, activated B cells, naive T cells, as well as central memory T cells (Jourdan et al., 2000, *J Immunol.* 165:716–24; Sozzani et al., 1998, *J Immunol.* 161:1083–6; Yanagihara et al.,1998, *J Immunol.* 161:3096–102; Yoshida, et al., 1998, *Int Immunol.* 10:901–10). CCR7 and its ligands are key regulators in cellular trafficking to the lymph nodes and other secondary lymphoid organs (SLO).

CCR7 responds to two CC chemokines: SLC (also called (CCL21, 6Ckine, TCA4, and Exodus 2) and ELC (also CCL19, MIP3 beta, EB 1 ligand, and CKb11). Experiments in CCR7 knockout mice have indicated that CCR7 plays an important role in organizing the primary immune response (Forster et al., 1999, *Cell* 99:23–33). Both CCR7 and its ligands play a significant role organizing the events which are required to generate an efficient primary immune response especially by facilitating co-localization of antigen presenting cells and immune effector cells by inducing their migration to secondary lymph organs (SLOs). Expression of CCR7 on cells infected with engineered virus results in homing of these cells to SLO where CCR7 ligands, ELC and SLC are expressed, i.e., specifically in areas where antigen presentation and immune education take place. Alternatively CCR7 on membrane of viral particles can lead free virus in the lymph to adhere to these regions through GAG bound ELC/SLC and hence be able to initiate an immune response.

The role of CCR7 and its ligands in cellular trafficking to the lymph nodes and other secondary lymphoid organs is described in, for example, Iwasaki et al., 2000, *J Exp Med* 191:1381–94; Forster et al., 1999, *Cell* 99:23–33; Sallusto et al., 1999, *Eur J Immunol* 29:1617–25; Kellermann et al., 1999, *J Immunol* 162:3859–64; Saeki et al., 1999, 162:2472–5; Dieu et al., 1998, *J Exp Med* 188:373–86; Gunn et al., 1999, *J Exp Med* 189:451–60.

4.1.2 ELC/SLC: ELC and SLC are CCR7 ligands. These chemokines are capable of inducing a calcium response in CCR7-expressing cells, and cells expressing CCR7 will migrate to a gradient of ELC or SLC (Yoshida et al., 1997, *J Biol Chem.* 272:13803–9; Yoshida et al., 1998, *J Biol Chem.* 273:7118–22. Both SLC and ELC are constitutively expressed in secondary lymph organs. ELC and SLC have also been shown to bind only one other receptor originally and provisionally identified as CCR11 (Gosling et al., 2000, *J Immunol.* 164:2851–6).

4.1.3 MIP3α: MIP3α (also known as LARC, Exodus, or CCL20) is the ligand for CCR6, forming an exclusive receptor/ligand pair (Baba et al., 1997, *J Biol Chem.* 272:14893–8). Immature dendritic cells expressing CCR6 can also be generated in vitro from monocytes stimulated with TGF-beta 1 (Yang et al., 1999, *J Immunol.* 163:1737–41). Expression of MIP3α at specific anatomical sites is believed to induce influx of CCR6 bearing immature dendritic cells, hence enhancing localization and priming of these key antigen presenting cells (Dieu et al., 1998, *J Exp Med.* 188:373–86). Thus, expression of MIP3 α by infected cells, either secreted or surface bound, is believed to cause targeting by immature dendritic cells which express CCR6. Without intending to be bound by a particular mechanism, virally infected cells expressing MIP3α attract APC, which take up virus-encoded antigen, mature and then migrate to SLO to stimulate immunity. CCR6, the only known receptor for MIP3α, is expressed in vivo predominately on the surface of lymphocytes and resident Langerhan cells (i.e., skin dendritic) (Greaves et al., 1997, *J Exp Med.* 186:837–44). A GenBank Accession no. is Xm 004279.

4.1.4. MIP1β: Human MIP1beta (accession number J04130, Lipes et al., 1988, *Proc. Natl. Acad. Sci. U.S.A.* 85:9704) is a CC chemokine and has a murine homologue (Graham et al., 1990, *Nature Vol.* 344:442). It has highly selective chemoattractive activity to monocyte derived immature dendritic cells (see, e.g., PCT Application No. 01/12162, filed Apr. 12, 2001).

4.1.5. MC10: Mouse C10 is a CC chemokine (Accession number AF293362) with no known human counterpart (Orlofsky et al, 1991, *Cell Regulation,* 2:403–12) and is expressed primarily from mouse macrophage cells. It has homology to the MIP1 family (Orlofsky, A et al, *Cell Regulation,* Vol 2, p403–412, 1991). Highly selective in vitro migratory activity on human monocyte-derived immature dendritic cells has been demonstrated (see, e.g., PCT Application No. 01/12162, filed Apr. 12, 2001).

4.1.6 mMDC: (Accession number AF076596) is a member of the murine CC chemokine family produced by activated B lymphocytes and dendritic cells (Schaniel et al, 1998, *J Exp. Med.,* 188:451–63) and has a human homologue called MDC (Godiska et al, *J. Exp. Med.* 185:1595–1604). The human version has been reported to have activity towards monocytes, monocyte-derived dendritic cells, and natural killer cells (Godiska, supra). Certain of the inventors have shown, however, that in in vitro assays, murine MDC has selective activity towards human monocyte-derived immature dendritic cells (see, e.g., PCT Publication WO 01/80887.

TABLE 3

Exemplary Non-Viral Chemokine Elements

| Chemokine element | GenBank Accession No. |
|---|---|
| CCR7 | XM 008651 |
| MIP3α | XM 002224 |
| ELC | XM 005637 |

TABLE 3-continued Exemplary Non-Viral Chemokine Elements

| Chemokine element | GenBank Accession No. |
|---|---|
| SLC | XM 005633 |
| MIP1β | J04130 |
| C10 | AF293362 |
| MDC | AF076596 |

4.2 Introduction of Heterologous Chemokine Elements into Virus

With certain modified CMV compositions which are provided, a heterologous chemokine element (e.g., human chemokine or chemokine receptor gene) is introduced into the virus genome along with regulatory elements that permit expression of the chemokine element in infected cells (i.e., on the surface of infected cells, secreted by infected cells, and/or on the surface of virions produced in infected cells). This can be accomplished in a variety of ways routine in the molecular biology arts, including, for example, by using an expression cassette. To express the gene product of interest, the coding sequence is operably linked to a promoter sequence. In addition, when the encoded protein is to be secreted by the cell, a secretion leader sequence is included. The secretion leader sequence may be naturally associated with the introduced gene (e.g. for genes encoding naturally secreted products) or may by synthetic or heterologous (e.g., inserted into the DNA sequence at the protein or peptide amino-terminus to encode a fusion protein). See, e.g., Ausubel, supra, and Sambrook, supra.

Suitable promoters are typically constitutive, but may be constitutive, cell type-specific, stage-specific, and/or modulatable or regulatable (e.g., by hormones such as glucocorticoids). Useful promoters include, but are not limited to, the metallothionein promoter, the constitutive adenovirus major late promoter, the dexamethasone-inducible MMTV promoter, the SV40 promoter, the MRP polIi promoter, the constitutive MPSV promoter, the tetracycline-inducible CMV promoter (such as the human immediate-early CMV promoter), the constitutive CMV promoter, and promoter-enhancer combinations known in the art. As noted supra, other regulatory elements may also be required or desired for efficient expression of a polynucleotide and/or translation of a sequence encoding proteins. For translation, these elements typically include an ATG initiation codon and adjacent ribosome binding site or other sequences. For sequences encoding full-length proteins or fragments including the initiation codon, no additional translational signals may be needed. However, in cases where only a protein fragment is inserted, exogenous transcriptional and/or translational control signals (e.g., the promoter, ribosome-binding site, and ATG initiation codon) must often be provided. In addition, the efficiency of expression may be enhanced by the inclusion of enhancers appropriate to the host or cell system in use. For example, the SV40 enhancer or CMV enhancer may be used to increase expression. Additionally, a poly A sequence can also be included.

As noted supra, in some embodiments targeting substitutions of endogenous viral chemokine and chemokine receptor genes are replaced with exogenous (e.g., human) chemokine and chemokine receptor genes, for example: US28→CCR7;vCXC1 (UL146) and/or vCXC2 (UL147) →ELC and/or SLC ("→"=replaced with).

5. Immunogen Expression 5.1 Choice of Immunogen

Exemplary pathogens (or agents) and genes encoding antigens are provided in Table 4 and additional examples of immunogens are described infra. According to the invention, the immunogenic polypeptide is characteristic of a pathogenic organism (e.g., virus, bacterium, fungus, parasite or protozoan) or is a tumor antigen. Candidate immunogens are those for which it is known, believed, expected or proposed that, if elicited, an immune response to the immunogen in an animal would be therapeutic or protective from disease. Thus, antigens not associated with pathogenic organisms, such as reporter genes (e.g., SEAP, GFP; β-glucuronidase; His6 reporter tag), antibiotic resistance genes used in genetic engineering (e.g., resistance to chloramphenicol, kanamycin, G418, bleomycin and hygromycin), and the like are usually not suitable as immunogens for the present compositions.

It will be appreciated that it is not necessary (or always desirable) to express the entire polypeptide encoded by a pathogen, and typically, one or more an immunogenic fragments of the polypeptides are expressed. When fragments are used, suitable immunogenic sequences are known or can be determined using routine art-known methods. See, e.g., Ausubel chapter 11.15. Typically, the expressed immunogenic polypeptide is at least 6 amino acids in length, more often at least about 8, and sometimes at least about 10, at least about 20, at least about 50 residues, or even full-length. In some instances, the immunogenic polypeptide is expressed as a fusion polypeptide.

TABLE 4

| Exemplary Antigens | | |
|---|---|---|
| Pathogen/ Biothreat Agent | Gene | GenBank Accession No. |
| Bacillus anthracis | PA (protective antigen) | M22589 |
| Dengue | NS1 | M58486 |
| Yersinia pestis | F1 | X61996 |
| Ebola | GP | U31033 |
| | NP | J04337 |
| Marburg | GP | X68493 |
| | NP | X68495 |
| Lassa | N | K03362 |
| | GPc | J04324 |
| Venezulean equine encephalitis virus (VEE) | GP | L04598 |
| Eastern equine encephalitis virus (EEE) | GP | D00145 |

Additional exemplary antigens or vaccine components include antigens derived from microbial pathogens such as bacteria (e.g., Pertussis, Cholera, Meningitis, *Borrelia burgdorferi,* Haemophilus B, *Streptococcs pneumoniae,* Typhoid), and viruses (e.g., in addition to Herpes viruses, e.g., Influenza virus; Hepatitis A; Hepatitis B; Measles; Rubella virus; Mumps, Rabies; Poliovirus; Japanese Encephalitis virus; Rotavirus; Varicella; and Smallpox), Diphtheria (*Corynebacterium diphtheriae*) and Tetanus (*Clostridium tetani*). Other antigens are derived from parasites. In an embodiment, the antigen is a tumor associated antigen (tumor specific antigen) and the reagents of the invention are used to treat cancers, including, but not limited to, melanomas, lung cancers, thyroid carcinomas, breast cancers, renal cell carcinomas, squamous cell carcinomas, brain tumors and skin cancers.

Expression of a desired sequence can be accomplished using routine methods for, e.g., expressing a selected sequence in a mammalian cell. Promoters such as those described supra, §4.3, can be used to express an immunogenic protein. Multicistronic constructs or fusion protein-encoding sequences can also be used in the construction of the recombinant viruses.

6. Administration of Immunogenic Compositions 6.1 CMV Strains

Typically, the CMV strain that is modified for use in the methods provided herein is matched to the intended host. For example, a vaccine intended for use in human subjects uses a human CMV (modified as described herein), such as CMV AD169, CMV Towne, CMV Davis, CMV Toledo. Similarly, for a vaccine intended for use in Rhesus monkeys, a monkey CMV (modified as described herein), such as CMV Rh68.1, CMV CSG is used. In any event, the virus used in formulation of a vaccine should be able to infect at least some cells of the host organism.

6.2 Formulation and Administration

When used for vaccination, vaccination with the compositions of the invention may be prophylactic vaccination (wherein the vaccine is administered prior to exposure, or anticipated exposure, to the target antigen, e.g., to a subject susceptible to or otherwise at risk of exposure to a disease) and/or immunotherapeutic vaccination (wherein the vaccine is administered after exposure to the target antigen to accelerate or enhance the immune response).

The vaccine preparations of the invention are typically administered intradermally or subcutaneously, but can also be administered in a variety of ways, including orally, by injection (e.g., intradermal, subcutaneous, intramuscular, intraperitoneal and the like), by inhalation, by topical administration, by suppository, using a transdermal patch.

When administration is by injection, the compositions may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

In some instances, multiple preparations of recombinant viruses (e.g., each encoding and expressing a different antigen or immunogenic polypeptide) can be administered.

Typically, an amount of the viral composition will be administered to the subject that is sufficient to immunize an animal against an antigen (i.e., an "immunologically effective dose" or a "therapeutically effective dose"). The effective dose can be formulated in animal models to achieve an induction of an immune response using techniques that are well known in the art. Exemplary doses are 10 to $10^7$ pfu per dose, e.g., 10 to $10^6$ or $10^3$ to $10^6$ pfu. One having ordinary skill in the art can readily optimize administration to humans (e.g., based on animal data and clinical studies).

In various embodiments, the compositions include carriers and excipients (including but not limited to buffers, carbohydrates, mannitol, proteins, polypeptides or amino acids such as glycine, antioxidants, bacteriostats, chelating agents, suspending agents, thickening agents and/or preservatives), other pharmaceutically acceptable auxiliary substances as required to approximate physiological conditions, such as buffering agents, tonicity adjusting agents, wetting agents and the like, and/or a conventional adjuvant (e.g., Freund's Incomplete Adjuvant, Freund's Complete Adjuvant, Merck Adjuvant 65, AS-2, alum, aluminum phosphate, mineral gels such as aluminum hydroxide, and surface active substances such as lysolecithin, pluronic polyols, polyanions, peptides, oil emulsions, keyhole limpet hemocyanin, and dinitrophenol). It will be recognized that, while any suitable carrier known to those of ordinary skill in the art may be employed to administer the compositions, the type of carrier will vary depending on the mode of administration. Compounds may also be encapsulated within liposomes using well known technology.

The compositions are usually produced under sterile conditions and may be substantially isotonic for administration to hosts. Typically, the compositions are formulated as sterile, and in full compliance with all Good Manufacturing Practice (GMP) regulations of the U.S. Food and Drug Administration.

7. EXAMPLES 7.1 General Virology Methods

General methods handling CMV, and for constructing CMV genomic mutants are known to practitioners of the virology art. See, e.g., Mocarski et al., 1996, *Intervirology* 39:320–30, 1996; Spaete et al, 1987, *Proc. Natl. Acad. Sci. USA* 84:7213–17; Ehsani et al, 2000, *J Virol,* 74:8972–79.

7.1.1 Viral DNA Preparation

Viral DNA can be prepared from infected cells using the method of Ehsani et al., 2000, *J Virol* 74:8972–9, or other suitable methods.

7.1.2 Propagation of Virus and Cells

Virus and cells are propagated by standard methods. Human CMV is propagated in human fibroblasts, e.g., human dermal fibroblast (HDF, Clonetics, CA), MRC-5 (ATCC #CCL 171) and others, grown in Dulbecco's minimal essential medium (DMEM) with 10% fetal bovine serum supplemented with amino acids and antibiotics according to standard techniques (Spaete and Mocarski, 1985, *J . Virology* 56:135–43). Murine CMV is propagated in mouse fibroblasts, e.g. NIH/3T3 embryonic mouse fibroblasts (ATCC No. CRL-1658) and others, grown in Dulbecco's minimal essential medium (DMEM) with 10% fetal bovine serum supplemented with amino acids and antibiotics according to standard techniques. Rhesus CMV is propagated in rhesus fibroblasts, e.g. DBS-FRhL-2 rhesus lung fibroblasts (ATCC No. CL-160) and others, grown in DMEM with 10% fetal bovine serum supplemented with amino acids and antibiotics as per standard techniques.

7.2 Example 1

Simultaneous Knock-Out of Viral Gene and Insertion of Heterologous Chemokine Element into a CMV Genome This example describes a general protocol for the construction of the recombinant cytomegaloviruses described in the application. The recombinants may include 1) disabled viral chemokine element or immune-modulatory genes 2) insertion of a heterologous gene encoding a chemokine element 3) insertion of a foreign antigen gene or 4) combinations of the above.

In one embodiment the viral (e.g., CMV) gene to be disabled is replaced with a gene encoding a heterologous chemokine element, a heterologous antigen gene and/or a selectable marker by constructing a targeting plasmid vector. The targeting vector contains the heterologous chemokine element, a heterologous antigen gene and/or a selectable marker operably linked to regulatory sequences and flanked by sequence from the viral gene (typically at least 300, and often at least 500, base pairs of viral sequence is present at each end of the insert, i.e., the 5' and 3' ends). In constructing the targeting vector, one suitable approach is to clone the viral gene into a (plasmid) vector and insert an expression cassette encoding the entire heterologous chemokine element, a heterologous antigen gene and/or a selectable marker with or without the removal of CMV sequence. It will be apparent to one of ordinary skill that these constructs can be prepared using routine molecular biological techniques, e.g., insertion of synthetic, amplified or subcloned gene fragments of interest into existing restriction sites in a target sequence; introduction of additional restriction sites using synthetic linkers, site-directed mutagenesis; and the like.

Regulatory sequences typically include a promoter active in cells of the host (e.g. the CMV major immediate early promoter, CMV MIEP), an internal ribosome entry site (IRES) (e.g. the EMC IRES), a selectable marker (e.g. the puromycin resistance gene, green fluorescent protein, etc.), and a polyadenylation signal (e.g. the SV40 polyadenylation signal).

In an alternate approach sequence encoding the heterologous chemokine element, a heterologous antigen gene and/or a selectable marker may be inserted into an inter-genic space with or without the removal of CMV sequence. Appropriate loci may include but are not limited to the inter-genic space between CMV US1 and US2, UL108 and UL109 and other loci. Sequence is inserted by construction of a targeting vector. The targeting vector contains the heterologous chemokine element, a heterologous antigen gene and/or a selectable marker operably linked to regulatory sequences and flanked by sequence from the viral gene (typically at least 300, and often at least 500, base pairs of viral sequence is present at each end of the insert, i.e., the 5' and 3' ends). In constructing the targeting vector, one suitable approach is to clone the viral loci into a (plasmid) vector and insert an expression cassette entire encoding the heterologous chemokine element, a heterologous antigen gene and/or a selectable marker with or without the removal of CMV sequence. It will be apparent to one of ordinary skill that these constructs can be prepared using routine molecular biological techniques, e.g., insertion of synthetic, amplified or subcloned gene fragments of interest into existing restriction sites in a target sequence; introduction of additional restriction sites using synthetic linkers, site-directed mutagenesis; and the like.

Regulatory sequences typically include a promoter active in cells of the host (e.g. the CMV major immediate early promoter, CMV MIEP), an internal ribosome entry site (IRES) (e.g. the EMC IRES), a selectable marker (e.g. the puromycin resistance gene, green fluorescent protein, etc.), and a polyadenylation signal (e.g. the SV40 polyadenylation signal).

In an alternate strategy the foreign gene may be inserted into a recombinant genome at the same locus as a previous insertion. For instance the heterologous chemokine element, a foreign antigen gene and/or a selectable marker may be targeted to replace the selectable marker used in the previous insertion of another heterologous gene (e.g., a chemokine element). Sequence is inserted by construction of a targeting vector. The targeting vector contains the heterologous chemokine element, a heterologous antigen gene and/or a second selectable marker operably linked to regulatory sequences and flanked by sequence from the first selectable marker or regulatory element (typically at least 300, and often at least 500, base pairs of viral sequence is present at each end of the insert, i.e., the 5' and 3' ends). In constructing the targeting vector, one suitable approach is to clone sequence from the first selectable marker into a (plasmid) vector and insert an expression cassette encoding the heterologous chemokine element, a heterologous antigen gene and/or a selectable marker with or without the removal of selectable marker sequence. It will be apparent to one of ordinary skill that these constructs can be prepared using routine molecular biological techniques, e.g., insertion of synthetic, amplified or subclone gene fragments of interest into existing restriction sites in a target sequence; introduction of additional restriction sites using synthetic linkers, site-directed mutagenesis; and the like.

CMV recombinants are generated by co-transfection of the targeting vector and wild type CMV viral DNA or recombinant CMV viral DNA into dermal fibroblasts of the appropriate species (e.g., human dermal fibroblasts, rhesus dermal fibroblasts, murine 3T3 fibroblasts) using calcium phosphate transfection. Cells containing recombinant virus are purified from wild type infected cells by selection with antibiotic, colormetric selection, or the like. Selected infected cells are then subjected to plaque purification by standard techniques to obtain a pure recombinant virus preparation.

The purified virus preparation is then combined with a suitable carrier (e.g., physiological saline containing a stabilizer) for administration to a host animal.

7.3 Example 2

Simultaneous Knock-Out of Human CMV US28 Gene and Insertion of Human CCR7 Coding Sequence This example describes production of human CMV recombinants in which US28 has been disabled and human CCR7 coding sequences operably linked to a promoter have been inserted.

Using viral DNA extracted from human CMV strain AD169 (Genbank Accession no. x17403) virions as template, PCR amplification is carried out using the primers: gtgaattcggttggttccccgtgttt (SEQ ID NO:11) (AD27up) and gcggatcctcgcgagtcgcgtcttcatcgtag (SEQ ID NO:12) (AD28low) to amplify AD27/28. The resulting 822 bp fragment is purified, digested with BamHI and EcoRI, and cloned into BamHI and EcoRI digested vector (pGEM3 (Promega)). The resulting construct is called pGEM28.1.

Using the same viral DNA template as above, PCR amplification is carried out using the primers: gtggatcctcgagcgctcgcctttttgtcact (SEQ ID NO:13) (AD28up) and gcggatccccccgcccaccatacaac (SEQ ID NO:14) (AD29low) to amplify AD27/28. The resulting 877 bp fragment is purified, digested with BamHI, cloned into pGEM28.1, cut with BamHI with the end homologous to AD28up juxtaposed to sequence homologous to AD28low. The resulting construct is called pGEM28.2.

To clone the human CCR7 receptor (CCR7 mRNA sequence, Genbank Accession no. XM 049959), whole cell RNA is isolated from human PBMC (e.g. using commercially available kits, Qiagen, Calif.). PCR amplification is carried out using the primers: gcgaattcagcgtcatggacctgggg (SEQ ID NO:15) (ccr7up) and tggaattcagaagagtcgcctatggg (SEQ ID NO:16) (ccr7low) to amplify CCR7.1. The resulting 1172 bp product is purified, digested with EcoRI, and cloned into pIRESpuro (Clontech) at the EcoRI site. The resulting construct is called pIRES CCR7.1.

pIRES CCR7.1 is digested with NruI and XhoI. The 3861 bp restriction fragment contains (5' to 3') the CMV major immediate early promoter (CMV MIEP) CCR7 coding sequence, the EMC internal ribosome entry site (IRES), the puromycin resistance gene, and the SV40 polyadenylation signal. This fragment is cloned into pGEM28.2 digested with NruI and XhoI. The resulting construct is called pGEM28 CCR7. These steps remove 771 bp of CMV US28, and insert a 3861 bp fragment containing CMV MIEP/CCR7/IRES/puro/polyA (i.e., 3090 bp total insertion).

CMV recombinants are generated by co-transfection of this vector (pGEM28 CCR7) and wild type CMV viral DNA into human dermal fibroblasts (Clonetics) using calcium phosphate transfection. Cells containing recombinant virus are purified from wild type infected cells by selection with the antibiotic puromycin. Selected infected cells are then subjected to plaque purification by standard techniques to attain a pure recombinant virus preparation.

7.4 Example 3

Simultaneous Knock-Out of Murine CMV UL78 Gene and Insertion of Murine CCR7 Coding Sequence This example describes production of murine CMV recombinants in which UL78 has been disabled and murine CCR7 coding sequences operably linked to a promoter and selectable marker have been inserted.

Using viral DNA extracted from murine CMV (e.g., strain Smith (Genbank Accession no. U68299)) virions as template, PCR amplification is carried out using the primers: ataagaatgcggccgctcgactacatgctgctgc (SEQ ID NO:17) (S78.1) and cggaattccgtccggctgctgcgcttcttc (SEQ ID NO:18) (S78.2). The 2351 bp PCR fragment is isolated and digested with NotI and EcoRI, and cloned into NotI and EcoRI digested vector (pGEM11 (Promega)). The resulting construct is called pGEMm78.

To clone the murine CCR7 receptor (mCCR7 mRNA sequence, Genbank Accession no. NM_007719), murine genomic DNA is isolated from murine PBMC (e.g. using commercially available kits, Qiagen, Calif.). PCR amplification is carried out using the primers: ataagaatgcggccgct-gacccagggaaaccagg (SEQ ID NO:19) (mCCR7up) and cggaattccgtcagctcctgggagaggtccttg (SEQ ID NO:20) (mCCR7low) to amplify mCCR7. This fragment is digested with NotI and EcoRI and cloned into NotI and EcoRI digested pIRESpuro (Clontech) to give pIRESpuromCCR7. The pIRESpuromCCR7 vector construct is digested with NruI and XhoI, generating a DNA fragment which encodes the CMV major immediate early promoter (CMV MIEP), mCCR7 coding sequence, the EMC internal ribosome entry site (IRES), the puromycin resistance gene, and the SV40 polyadenylation signal. The purified NruI-XhoI fragment is then cloned into the pGEMm78 vector digested with SmaI and XhoI. These sites are compatible with the NruI and XhoI sites of the mCCR7 fragment for ligation. The resulting construct (pGEMm78IRESmCCR7) contains the m78 gene disrupted by the insertion of the mCCR7 gene and an IRES driven puromycin selection marker.

CMV recombinants are generated by co-transfection of this vector (pGEMm78IRESmCCR7) and wild type murine CMV (e.g., strain Smith) viral DNA into murine 3T3 fibroblasts (ATCC #CCL92) using calcium phosphate transfection. Cells containing recombinant virus are purified from wild type infected cells by selection with the antibiotic puromycin. Selected infected cells are then subjected to plaque purification by standard techniques to attain a pure recombinant virus preparation.

7.5 Example 4

Insertion of Bacillus Anthracis Protective Antigen Gene into US28/CCR7 Recombinant CMV This example describes insertion of a Bacillus anthracis protective antigen gene into the genome of the US28/CCR7 recombinant CMV described in Example 2.

Using viral DNA extracted from human CMV strain AD169 (Genbank Accession no. x17403) virions as template, PCR amplification is carried out using the primers: gcggtaccgcgacgccgtcgctggg (SEQ ID NO:21) (108 up) and tggatccgtcagggaaatacaag (SEQ ID NO:22) (108 low) to amplify AD108. The resulting 1300 bp fragment is purified, digested with BamHI and KpnI, and cloned into BamHI and KpnI digested vector (pGEM3 (Promega)). The resulting construct is called pGEM108.

Using the same viral DNA template as above, PCR amplification is carried out using the primers: atggatcctct-tctatcacggtggc (SEQ ID NO:23) (109 up) and gcggatccag-gatcgatttcgtgcg (SEQ ID NO:24) (109 low) to amplify AD109. The resulting 1085 bp fragment is purified, digested with BamHI, and cloned into pGEM108 cut with BamHI with the end homologous to AD109up juxtaposed to sequence homologous to AD108low. The resulting construct is called pGEM108/109.

To clone the Bacillus anthracis protective antigen (BAPA; Genbank Accession no. M22589), DNA is isolated from bacilli containing the BAPA sequence (e.g., pBLSCR-PPA from Iacono-Connors L.C. at U.S. Army Medical Research Institute of Infectious Diseases, Frederick Mass.) by routine means (e.g. using commercially available kits from Qiagen, Calif.) and used as template for PCR with the primers ggcccggggaagttaaacaggagaaccg (SEQ ID NO:25) (BAPAup) and gggatatcttaccttatcctatctcat (SEQ ID NO:26) (BAPAlow). The resulting 2229 bp product is purified, cut with EcoRV and XmaI, and cloned into EcoRV and XmaI-digested vector (Clontech pIREShyg2). The resulting construct is called pBAPAiresHyg.

The following complimentary oligo sequences containing the Ig kappa leader sequence (Acc#D84070) are synthesized: '5'-ctagcatggagacagacacactcctgc tatgggtactgctgctctgggttccaggttccactggtgaccc-3' (SEQ ID NO:27)

5'-ccggggtcaccagtggaacctggaacccagagcagcagtacccata gcaggagtgtgtctgtctccatg-3' (SEQ ID NO:28)

and annealed to give a double-stranded oligonucleotide with overhangs for the restriction enzymes NheI and a XmaI. This synthetic sequence is cloned into NheI and XmaI-digested pBAPAiresHyg. The resulting construct is called pSecBAPAiresHyg.

pSecBAPAiresHyg is digested with XhoI then subjected to a partial digest with NruI. The 5560 bp restriction fragment contains (5' to 3') the CMV major immediate early promoter (CMV MIEP), the Ig kappa leader sequence, the BAPA coding sequence, the EMC internal ribosome entry site (IRES), the hygromycin resistance gene, and the SV40 polyadenylation signal. This fragment is cloned into pGEM108/109 digested with NruI and XhoI. The resulting construct is called pGEM108/109 BAPA. These steps remove 1058 bp of CMV inter-genic sequence between the AD169 UL108 and UL109 ORFs, and insert a 5560 bp fragment containing CMV MIEP/secreted BAPA/IRES/hygro/polyA (i.e., 4502 bp total insertion).

Viral DNA is purified from virions following infection of human dermal fibroblasts with a recombinant CMV strain prepared as described in Examples 1–3. CMV double recombinants are generated by co-transfection of this vector (pGEM108/109 BAPA) and the recombinant CMV viral DNA into human dermal fibroblasts (Clonetics) by calcium phosphate precipitation. Cells containing double recombinant virus are purified from wild type infected cells by selection with an antibiotic (e.g. hygromycin). Selected infected cells are then subjected to plaque purification by standard techniques to attain a pure double recombinant virus preparation.

7.6 Example 5

Simultaneous Knock-Out of Rhesus CMV UL33 Gene and Insertion of a Foreign Antigen Gene This example describes production of rhesus CMV recombinants in which rhesus UL33 has been disabled and rhesus CCR7 coding sequences operably linked to a promoter have been inserted.

Using viral DNA extracted from rhesus CMV (e.g., strain Rh68.1 (ATCC #VR 677)), virions as template, PCR amplification is carried out using the primers: cggaattcctctttagtcg-gcagggtctt (SEQ ID NO:29) (Rh32up) and ctggatccgtg-gctttgtctttggctttt (SEQ ID NO:30) (Rh33low) to amplify Rh32/33. The resulting 1404 bp fragment is purified, digested with BamHI and EcoRI, and cloned into BamHI and EcoRI digested vector (pGEM3 (Promega)). The resulting construct is called pGEM32-33.

To clone the *Bacillus anthracis* protective antigen (BAPA; Genbank Accession no. M22589), DNA is isolated from bacilli containing the BAPA sequence or from a plasmid containing this sequence (e.g., pBLSCRPPA from Iacono-Connors L.C. at U.S. Army Medical Research Institute of Infectious Diseases, Frederick Mass.) by routine means (e.g. using commercially available kits from Qiagen, Calif.) and used as template for PCR with the primers ggcccggggaagttaaacaggagaaccg (SEQ ID NO:25) (BAPAup) and gggatatcttaccttatcctatctcat (SEQ ID NO:26) (BAPAlow). The resulting 2229 bp product is purified, cut with EcoRV and XmaI, and cloned into EcoRV and XmaI-digested vector (Clontech pIREShyg2). The resulting construct is called pBAPAiresHyg.

The following complimentary oligo sequences containing the Ig kappa leader sequence (Acc#D84070) are synthesized:

5'-ctagcatggagacagacacactcctgctatgggtactgctgctctgggttcc
aggttccactggtgaccc-3' (SEQ ID NO:27)

5'-ccgggggtcaccagtggaacctggaacccagagcagcagtacccatag
caggagtgtgtctgtctccatg-3' (SEQ ID NO:28)

and annealed to give a double-stranded oligonucleotide with overhangs for the restriction enzymes NheI and a XmaI. This synthetic sequence is cloned into NheI and XmaI-digested pBAPAiresHyg. The resulting construct is called pSecBAPAiresHyg.

pSecBAPAiresHyg is digested with XhoI then subjected to a partial digest with NruI. The 5560 bp restriction fragment contains (5' to 3') the CMV major immediate early promoter (CMV MIEP), the Ig kappa leader sequence, the BAPA coding sequence, the EMC internal ribosome entry site (IRES), the hygromycin resistance gene, and the SV40 polyadenylation signal. This fragment is blunted using Deep Vent or Klenow enzyme (New England Biolabs) to give a 5560 bp fragment containing CMV MIEP/secreted BAPA/IRES/hygro/polyA and cloned into pGEM32-33 digested with MscI and PshAI so as to remove the central portion of the rhesus UL33 ORF.

The resulting construct is called pGEM33 BAPA. These steps remove 852 bp of rhesus CMV UL33, and insert a 5560 bp fragment containing CMV MIEP/secreted BAPA/IRES/hygro/polyA (i.e., 4708 bp total insertion).

CMV recombinants are generated by co-transfection of this vector (pGEM33 BAPA) and wild type or recombinant rhesus CMV viral DNA into rhesus dermal fibroblasts using calcium phosphate transfection. Cells containing recombinant virus are purified from wild type infected cells by selection with an appropriate antibiotic (e.g., hygromycin). Selected infected cells are then subjected to plaque purification by standard techniques to attain a pure recombinant virus preparation.

7.7 Example 6

Alternative Virus Construction Strategy

This example describes an alternative cloning strategy for viral recombinants.

CMV (e.g., Rhesus) viral recombinants are constructed with modifications of UL111A and US28, and other genes using a yeast shuttle vector (e.g., see Larionov et al., 1996, *Proc Natl Acad Sci USA* 93:491–6). Rhesus CMV sequence (hooks) is inserted by standard bacterial cloning techniques, into CEN6+yeast shuttle vector pVC604 (recombinants are not viable in yeast as deficient in the yeast autonomous replicating sequence (ARS)). A pGEM vector containing sequence homologous to the gene of interest is constructed with early termination signals, a FLAG epitope tag and a yeast ARS incorporated in the ORF by PCR based mutagenesis. Spheroplast transformation of recombinagenic yeast strain VL6-48 with above vectors and viral genomic DNA using highly efficient TAR cloning methodologies (transformation associated recombination (Larionov et al, 1996, *Proc Natl Acad Sci USA* 93:491–6). Only triple recombination events are viable in yeast due to ARS/CEN6 selection. Retrofitting of yeast vector, using TAR, with a bacterial F factor origin of replication (with plasmid BRV-1 and His selection) allowing carriage and amplification of the vector in bacteria (chloramphenicol selection). Anion exchange isolation of vector DNA from bacteria and restriction enzyme mediated cleavage of non viral sequence leaves a viral DNA substrate. Calcium phosphate based transfection into rhesus DF generates a pure population of recombinant virus. Amplification of recombinants in rhesus DF is carried out in tissue culture for evaluation in vitro and in vivo.

7.8 Assays

7.8.1. Assay for CCR7 Targeting of Virions/Cells to Secondary Lymph Organs

In vivo assays to measure increased targeting of virus (CMV) engineered to express CCR7 to secondary lymph organs can be performed as follows. Typically, the assays are carried out in an animal model, e.g., non-human primates, e.g., baboons or Rhesus monkeys (*macaca mulatta*).

In an exemplary assay, Rhesus CMV strain 68.1 (e.g., $10^4$–$10^7$ pfu, usually $10^6$ pfu, in excipient) is administered by oral inoculation (or subcutaneous injection) to CMV-negative animals. "Experimental" animals, are inoculated with a recombinant CMV strain bearing CCR7, while "control" animals receive the parental "wild type" CMV strain Rh68.1.

The dissemination of CCR7+ and CCR7- virus or virus infected cells to SLO is determined. Suitable assays for detecting this spread include gross measurements of SLO size or quantitative PCR of viral DNA. In one suitable assay, DNA isolated from SLO (e.g., using commercially available kits from Qiagen, Calif.) is assayed for viral DNA by PCR using CMV specific primers. For example, in one embodiment, DNA is purified from rhesus macaque SLO, then used as template for nested PCR with primers able to amplify the RhCMV immediate early 2 gene (5' GCC AAT GCA TCC TCT GGA TGT ATT GTG A 3' (SEQ ID NO:31) and 5' TGC TTG GGG AAT CTC TGC AC 3' (SEQ ID NO:32) then 5' CCC TTC CTG ACT ACT AAT GTA C 3' (SEQ ID NO:33) and 5' TTG GGG AAT CTC TGC ACA AG 3' (SEQ ID NO:34)) (see, e.g., Tarantal et al. 1998, *J Infect Dis* 177:446–50). An increased titer of viral DNA in SLO tissues of animals infected with CCR7 knock in virus versus controls indicates CCR7 directed migration of virus or virus infected cells to SLO.

Migration can also be assayed by histology. Typically, tissue is fixed in paraformaldehyde and embedded in paraffin, or frozen in OCT for frozen sections (see, e.g., by Lun a, L. G., THE MANUAL OF HISTOLOGIC STAINING METHODS OF THE ARMED FORCES INSTITUTE OF PATHOLOGY, , McGraw-Hill, 3rd edition, 1968). Sections are stained using an antibody specific for CMV (e.g., rhCMV). An increased number of cells expressing viral antigen in SLO tissues of animals infected with CCR7 knock in virus versus controls indicates CCR7 directed migration of virus or virus infected cells to SLO.

7.8.2. Assay for induction of antigen (e.g., BAPA) specific IgG response

In vivo assays in an animal model are sometimes used to demonstrate host response to expression of foreign antigens by recombinant CMVs. The assays can be carried out in humans, but are more typically conducted in non-human primates, e.g., Rhesus monkeys (*macaca mulatta*) or baboons, or other mammal models (e.g., mice).

In an exemplary assay, Rhesus CMV (e.g., $10^4$–$10^7$ pfu, usually $10^6$ pfu, in excipient) is administered by oral inoculation (or subcutaneous injection) to CMV-negative animals. "Experimental" animals, are inoculated with a recombinant CMV strain bearing a gene encoding a foreign antigen (e.g., *Bacillus anthracis* protective antigen (BAPA)), while "control" animals receive the parental "wild type" CMV strain. At days 15 to 30 (preferably day 30) peripheral blood is drawn from inoculated animals and the serum tested for antibodies to antigen in a specific ELISA (e.g., for BAPA, the protocol of Little and Knudson, 1986, *Infection and Immunity* 52: 509–512 maybe used).

7.8.3 Assay for induction of antigen (e.g., BAPA) specific CD8 T cell response

In vivo assays in an animal model are used to demonstrate host response to expression of foreign antigens by recombinant CMVs. The assays can be carried out in humans, but are more typically conducted in non-human primates, e.g., Rhesus monkeys (*macaca mulatta*) or baboons.

In an exemplary assay, Rhesus CMV (e.g., $10^4$–$10^7$ pfu, usually $10^6$ pfu, in excipient) is administered by oral inoculation (or intravenous injection) to CMV-negative animals. "Experimental" animals, are inoculated with a recombinant CMV strain bearing a gene encoding a foreign antigen, while "control" animals receive the parental "wild type" CMV strain. At days 15 to 30 (preferably day 30) peripheral blood is drawn from inoculated animals.

Ficoll purified PBMC are obtained from experimental and control animals and are resuspended and placed in 96-well microtiter plates coated with anti-monkey IFN_mAb MD-1 (U-Cytech, Utrecht, Netherlands). PBMC are plated in duplicate at two-fold dilutions ranging from 5 to $0.3 \times 10^5$ cells per well.

PBMC are infected with vaccinia recombinants expressing BAPA, as well as with control vaccinia at a moi of 10 PFU/cell at 37° C. in a 5% $CO_2$ incubator. After 16 to 24 hours, cells are removed by extensive washing and the wells were serially incubated with a biotinylated anti-monkey IFN_detector antibody (U-Cytech), followed by gold-labeled anti-biotin IgG (U-Cytech). An activator mix (U-Cytech) is added which allowed formation of silver salt precipitates at the sites of gold clusters. Spots are counted on a Zeiss ELISPOT imaging system. BAPA expressing vaccinia are constructed as previously described (Iacono-Connors L. C. et al, *Infection and Immunity* 58: 366–372, 1990).

7.8.4 Assays for Inhibition of CMV Dissemination by Gene Knock Out

Animal models can be used to demonstrate reduction of CMV dissemination when viral dissemination genes are disabled. Typically, in vivo assays in an animal model are used to demonstrate reduction of CMV. Typically, the assays are conducted in non-human primates, e.g., Rhesus monkeys (*macaca mulatta*) or baboons. In an exemplary assay, Rhesus CMV strain 68.1 (e.g., 10—10 pfu, usually $10^6$ pfu, in excipient) is administered by oral inoculation (or intravenous injection) to CMV-negative animals. "Experimental" animals, are inoculated with a recombinant CMV strain, while "control" animals receive the parental "wild type" CMV strain.

Rhesus is a favored model system for analysis. Rhesus CMV is able to replicate in human foreskin fibroblasts and conversely HCMV in primary chimpanzee fibroblasts (Perot et al., 1992, *J Gen Virol.* 73:3281–84) suggesting the close relatedness of the human and primate viruses. In addition certain of the inventors have shown that rhesus CMV is largely co-linear with HCMV, individual ORFs are largely homologous (50–65%) and peptides share up to 90% identity (Lockridge et al., 2000, *Virology* 268:272–80; Barry et al., 1996, *Virology* 215:61–72, 218:296). Furthermore the natural history of infection as well as characteristics of persistence and pathogenesis mirror those of HCMV (Lockridge et al., 1999, *J Virol.* 73:9576–83. Tarantal et al., 1998, *J Infect Dis.* 177:446–50).

Viral infection and dissemination in experimental and control animals is determined by analyzing spread of the virus from the site of primary inoculation. See Saederup et al, 1999, *Proc. Nat. Acad. Sci. USA* 96:10881–86. Suitable assays for detecting CMV are described in Lockridge et al., 1999, *J Virol.* 73:9576–83. Sterile blood, saliva and urine samples are collected at the time of virus administration and thereafter periodically (e.g., every day or every 3 days) and assayed for virus. According to one suitable assay, viral titer is measured in saliva, urine and blood samples, by co-cultivation of serial dilutions of sterile samples with a cell permissive for CMV replication (e.g., rhesus dermal fibroblasts) for a period of about 2 weeks, and counting of viral plaques, using standard techniques (Spaete and Mocarski, 1985, *J Virol* 56:135–43). Inhibition of CMV dissemination is demonstrated by a 5-fold or greater (e.g., at least 10-fold) reduction in the overall titer of infectious virus in at least one, sometimes two or three of these fluids in experimental animals compared to control animals when assayed at timepoints after innoculation (e.g., 3, 6, 9, 12, or 15 days or 1 month following innoculation). Inhibition of CMV dissemination can alternatively be shown by a delay in appearance of detectable virus in at least one, sometimes two or three of the these fluids in experimental animals compared to control animals.

In another suitable assay, blood is assayed for viral DNA by PCR using CMV specific primers. For example, in one embodiment, DNA is purified from plasma (e.g., using commercially available kits from Qiagen, Calif.), then used as template for nested PCR with primers able to amplify the RhCMV immediate early 2 gene (5' GCC AAT GCA TCC TCT GGA TGT ATT GTG A 3' (SEQ ID NO:31) and 5' TGC TTG GGG AAT CTC TGC AC 3' (SEQ ID NO:32) then 5' CCC TTC CTG ACT ACT AAT GTA C 3' (SEQ ID NO:33) and 5' TTG GGG AAT CTC TGC ACA AG 3' (SEQ ID NO:34)) (see, e.g., Tarantal et al., 1998, *J Infect Dis* 177:446–50). Inhibition of CMV dissemination is demonstrated by a difference of viral titer or kinetics (as described supra) as assessed by levels of viral DNA in peripheral blood.

Assays for viral dissemination can also be carried out by direct detection of CMV in tissues including lung, spleen thymus, salivary gland, bone marrow, pancreas, kidney, tonsil, liver, parotid gland, esophagus and others. Thus, in embodiment, animals are necropsied 15 to 30 days after administration of virus (e.g., day 30) and complete tissue and blood samples taken. DNA is purified from tissue (e.g. using commercially available kits from Qiagen, Calif.), then used as template for nested PCR as described supra. Dissemination can also be assayed by histology. Typically, tissue is fixed in paraformaldehyde and embedded in paraffin, or frozen in OCT for frozen sections (see, e.g., by Luna, L. G., THE MANUAL OF HISTOLOGIC STAINING METHODS OF THE ARMED FORCES INSTITUTE OF PATHOLOGY, McGraw-Hill, 3rd edition, 1968). Sections are stained using an antibody specific for CMV (e.g., rhCMV). Inhibition of CMV dissemination is demonstrated by a difference of viral titer or kinetics (as described supra) as assessed by levels of viral antigens in specific tissues or organs of experimental animals compared to control animals.

In another suitable assay, levels of reactive leukocytes are assayed, e.g., by FACS analysis of blood samples. Suitable assays are described in Lockridge et al., *J Virol.* 73:9576–83, supra. Briefly, activated T cells are identified by dual fluorescent staining for CD3 (T cell marker, Pharmingen, clone SP34) and CD69 (very early activation marker, Becton Dickinson, clone L78) while memory T cells will be identified by dual fluorescent staining for CD3 (T cell marker, Pharmingen, clone SP34) and CD45RO (memory cell marker, Dako, clone UCHL1). Inhibition of CMV dissemination is demonstrated by fewer activated T cells or memory T cells in peripheral blood of experimental animals compared to control animals (e.g., at least about 30% or about 50% fewer, often at least 80% fewer when measured following administration (e.g., 3, 6, 9, 12, or 15 days or 1 month following administration of the agent).

It is understood that the examples and embodiments described herein are for illustrative purposes only and that various modifications or changes in light thereof will be suggested to persons skilled in the art and are to be included within the spirit and purview of this application and scope of the claims. Each and every publication, patent, and patent application cited herein are hereby incorporated by reference in their entirety for all purposes.

What is claimed is:

1. A recombinant cytomegalovirus (CMV), comprising an attenuated CMV genome which comprises a first heterologous nucleotide sequence encoding a heterologous chemokine element, and (ii) a second heterologous nucleotide sequence encoding an immunogenic polypeptide.

2. The recombinant CMV of claim 1, wherein the CMV genome is encapsulated in infectious form as a virion.

3. The recombinant CMV of claim 2, which is formulated as a composition, the composition comprising a pharmaceutically acceptable adjuvant, carrier, diluent or excipient.

4. The recombinant CMV of claim 2, wherein
   (a) the recombinant CMV is a recombinant HCMV;
   (b) the immunogenic polypeptide comprises an antigen from an organism that is pathogenic in humans or a human tumor antigen;
   (c) a viral chemokine element or a viral immune-modulatory gene is disabled, the viral chemokine element selected from the group consisting of US28, US27, UL33, UL78, UL146 and UL147, or a homolog thereof, and the viral immune-modulatory gene selected from the group consisting of UL111A, US3, US6, US11, US2, UL83, UL18 and UL40, or a homolog thereof; and
   (d) the heterologous chemokine element is selected from the group consisting MIP3α, SLC, MDC, MC10, MIP1β, ELC and CCR7 or a homolog thereof.

5. The recombinant CMV of claim 2, wherein
   (a) the recombinant CMV is a recombinant rhCMV;
   (b) the immunogenic polypeptide comprises an antigen from a pathogenic organism or a tumor antigen;
   (c) a viral chemokine element or a viral immune-modulatory gene is disabled, the viral chemokine element selected from the group consisting of rhUS28.1, rhUS28.2, rhUS28.3, rbUS28.4, rhUS28.5, rhUL33 and rhUL78, or a homolog thereof, and the viral immune-modulatory gene selected from the group consisting of rhUL111A, rhUS3, rhUS6, rhuS11, rhUS2, rhUL83 and rhUL40, or a homolog thereof; and
   (d) the heterologous chemokine element is selected from the group consisting of MIP3α, SLC, MDC, MC10, MIP1β, ELC and CCR7, or a homolog thereof.

6. The recombinant CMV of claim 2, wherein
   (a) the recombinant CMV is a recombinant MCMV;
   (b) the immunogenic polypeptide comprises an antigen from a pathogenic organism or a tumor antigen;
   (c) a viral chemokine element or a viral immune-modulatory gene is disabled, the viral chemokine element selected from the group consisting of MUL33, MUL78, MCK-1 and MCK-2, or a homolog thereof and the viral immune-modulatory gene selected from the group consisting of m144, m152, m04, m06, m138, or a homolog thereof; and
   (d) the heterologous chemokine element is selected from the group consisting of MIP3α, SLC, MDC, MC10, MIP1β, ELC and CCR7, or a homolog thereof.

7. The recombinant CMV of claim 1, wherein a viral dissemination gene of the attenuated CMV genome is disabled.

8. The recombinant CMV of claim 7, wherein the viral dissemination gene is a gene encoding a viral chemokine element or a viral immune-modulatory gene.

9. The recombinant CMV of claim 8, wherein
   the recombinant CMV is a recombinant human CMV (HCMV) or a recombinant murine CMV (MCMV); and
   the viral dissemination gene is a gene encoding a viral chemokine element selected from the group consisting of US28, US27, UL33, UL78, UL146, UL147, MCK-1 and MCK-2, or a homolog thereof.

10. The recombinant CMV of claim 8, wherein
    the recombinant CMV is a recombinant HCMV or a recombinant MCMV; and
    the viral dissemination gene is a viral immune-modulatory gene selected from the group consisting of UL111A, US3, US6, US11, US2, UL83, UL18, UL40, m144, m152, m04, m06 and m138, or a homolog thereof.

11. The recombinant CMV of claim 1, wherein the recombinant CMV has reduced virulence in a host that is selected from the group consisting of a non-human primate and commercial livestock.

12. The recombinant CMV of claim 1, wherein the recombinant CMV is a recombinant rhCMV.

13. The recombinant CMV of claim 1, wherein the recombinant CMV is a recombinant MCMV.

14. The recombinant CMV of claim 1, wherein the heterologous chemokine element is a mammalian chemokine element.

15. The recombinant CMV of claim 14, wherein the heterologous chemokine element is a chemokine ligand.

16. The recombinant CMV of claim 14, wherein the heterologous chemokine element is a chemokine receptor.

17. The recombinant CMV of claim 1, wherein the heterologous chemokine element is selected from the group consisting of MIP3α, SLC, MDC, MC10, MIP1β, ELC and CCR7, or a homolog thereof.

18. The recombinant CMV of claim 1, wherein the immunogenic polypeptide comprises an antigen from a pathogenic organism or a tumor antigen.

19. The recombinant CMV of claim 18, wherein the pathogenic organism is a bacterium, a virus or a parasite.

20. The recombinant CMV of claim 19, wherein the immunogenic polypeptide comprises a fragment of a polypeptide from an organism selected from the group consisting of *Bacillus anthracis*, Dengue, *Yersinia pestis*, Ebola, Marburg, Lassa, Venezulean Equine Encephalitis and Eastern Equine Encephalitis.

21. The recombinant CMV of claim 18, wherein the immunogenic polypeptide comprises a tumor antigen.

22. The recombinant CMV of claim 21, wherein the tumor antigen is selected from the group consisting of antigens associated with breast cancers, lung cancers, thryroid carcinomas, squamous cell carcinomas and renal cell carcinomas.

23. The recombinant CMV of claim 1, wherein the first and second heterologous nucleotide sequence are operably linked to different promoters.

24. A recombinant cytomegalovirus (CMV) comprising an attenuated CMV genome that comprises a heterologous nucleotide sequence encoding a heterologous chemokine receptor or ligand.

25. The recombinant CMV of claim 24, wherein the CMV genome is encapsulated in infectious form.

26. The recombinant CMV of claim 25, wherein a viral dissemination gene of the CMV genome is disabled.

27. The recombinant CMV of claim 26, wherein the disabled viral dissemination gene is a gene encoding a viral chemokine element.

28. The recombinant CMV of claim 26, wherein the disabled viral dissemination gene is a gene encoding a viral immune-modulatory gene.

29. The recombinant CMV of claim 24, wherein the chemokine element is a mammalian chemokine element.

30. A method for inducing an immune response in a mammalian host, the method comprising administering a composition to the host, wherein the composition comprises a recombinant cytomegalovirus (CMV) comprising an attenuated CMV genome that contains (i) a first heterologous nucleotide sequence encoding a heterologous chemokine element, and (ii) a second heterologous nucleotide sequence encoding an immunogenic polypeptide.

31. The method of claim 30, wherein the attenuated CMV genome has a disabled viral dissemination gene.

32. The method of claim 31, wherein the viral dissemination gene is a gene encoding a viral chemokine element or a viral immune-modulatory gene.

33. The method of claim 32, wherein
the recombinant CMV is a recombinant human CMV (HCMV) or a recombinant murine CMV (MCMV); and
the viral dissemination gene is a gene encoding a viral chemokine element selected from the group consisting of US28, US27, UL33, UL78, UL146, UL147, MCK-1 and MCK-2, or a homolog thereof.

34. The method of claim 32, wherein
the recombinant CMV is a recombinant HCMV or a recombinant MCMV; and
the viral dissemination gene is a viral immune-modulatory gene selected from the group consisting of UL111A, US3, US6, US11, US2, UL83, UL18, UL40, m144, m152, m04, m06 and m138, or a homolog thereof.

35. The method of claim 30, wherein the heterologous chemokine element is a mammalian chemokine element.

36. The method of claim 35 wherein the heterologous chemokine element is a chemokine ligand.

37. The method of claim 35, wherein the heterologous chemokine element is a chemokine receptor.

38. The method of claim 35, wherein the heterologous chemokine element is selected from the group consisting of MIP3α, SLC, MDC, MC10, MIP1β, ELC and CCR7, or homolog thereof.

39. The method of claim 30, wherein the immunogenic polypeptide comprises an antigen from a pathogenic organism or a tumor antigen.

40. The method of claim 39, wherein the pathogenic organism is a bacterium, virus or a parasite.

41. The method of claim 30, wherein
(a) the host is a human and the recombinant CMV is a recombinant HCMV;
(b) a viral chemokine element or a viral immune-modulatory gene is disabled, the viral chemokine element selected from the group consisting of US28, US27, UL33, UL78, UL146, UL147, or a homolog thereof, and the viral immune-modulatory gene selected from the group consisting of UL111A, US3, US6, US11, US2, UL83, UL18, UL40, or a homolog thereof;
(c) the heterologous chemokine element is selected from the group consisting of MIP3α, SLC, MDC, MC10, MIP1β, ELC and CCR7, or a homolog thereof; and
(d) the immunogenic polypeptide comprises an antigen from an organism that is pathogenic in humans or a human tumor antigen.

42. The method of claim 30, wherein
(a) the host is a rhesus monkey and the recombinant CMV is a recombinant rhCMV;
(b) a viral chemokine element or a viral immune-modulatory, gene is disabled, the viral chemokine element selected from the group consisting of rhUS28.1, rhUS28.2; rhUS28.3, rhUS28.4, rhUS28.5, rhUL33 and rhUL78, or a homolog thereof, and the viral immune-modulatory gene selected from the group consisting of rhUL111A, rhUS3, rhUS6, rhUS11, rhUS2, rhUL83 and rhUL40, or a homolog thereof;
(c) the heterologous chemokine element is selected from the group consisting of MIP3α, SLC, MDC, MC10, MIP1β, ELC and CCR7, or a homolog thereof; and
(d) the immunogenic polypeptide comprises an antigen from a pathogenic organism or a tumor antigen.

43. The method of claim 30, wherein
(a) the host is a mouse and the recombinant CMV is a recombinant MCMV;
(b) a viral chemokine element or a viral immune-modulatory gene is disabled, the viral chemokine element selected from the group consisting of MUL33, MUL78, MCK-1 and MCK-2, or a homolog thereof, and the viral immune-modulatory gene selected from the group consisting of m144, m152, m04, m06, m138 or a homolog thereof;
(c) the heterologous chemokine element is selected from the group consisting of MIP3α, SLC, MDC, MC10, MLP1β, ELC and CCR7, or a homolog thereof; and
(d) the immunogenic polypeptide comprises an antigen from a pathogenic organism or tumor antigen.

44. A therapeutic or prophylactic treatment method, the method comprising administering a composition to a mammal, wherein
(a) the composition comprises an attenuated recombinant cytomegalovirus (CMV) with a genome that comprises (i) a first nucleotide sequence encoding a chemokine receptor or chemokine that is endogenous to the mammal, and (ii) a second nucleotide sequence encoding an immunogenic polypeptide; and
(b) the immunogenic polypeptide comprises an antigen correlated with a disease or infection which the mammal has or is susceptible to obtaining; and whereby the administered composition induces an immune response in the animal.

45. The method of claim 44, wherein a viral dissemination gene of the CMV genome is disabled.

46. The method of claim 45, wherein the viral dissemination gene is a gene encoding a viral chemokine element.

47. The method of claim 46, wherein
the recombinant CMV is a recombinant human CMV (HCMV) or a recombinant murine CMV (MCMV); and
the gene encoding the viral chemokine element is selected from the group consisting of US28, US27, UL33, UL78, UL146, UL147, MCK-1 and MCK-2, or a homolog thereof.

48. The method of claim 45, wherein the viral dissemination gene is a gene encoding a viral immune-modulatory gene.

49. The method of claim 48, wherein
the recombinant CMV is a recombinant HCMV or a recombinant MCMV; and
the viral immune-modulatory gene is selected from the group consisting of UL111A, US3, US6, US11, US2, UL83, UL18, UL40, m144, m152, m04, m06 and m138, or a homolog thereof.

50. The method of claim 44, wherein the mammal is selected from the group consisting of a human, a non-human primate and commercial livestock.

51. The method of claim 44, wherein the mammal is selected from the group consisting of a non-human primate and a mouse.

52. The method of claim 44, wherein
(a) the animal is a human and the recombinant CMV is a recombinant HCMV;
(b) a viral chemokine element or a viral immune-modulatory gene is disabled, the vital chemokine element selected from the group consisting of US28, US27, UL33, UL78, UL146 and UL147, or a homolog thereof, and the viral immune-modulatory gene selected from the group consisting of UL111A, US3, US6, US11, US2, UL83, UL18, and UL40, or a homolog thereof; and
(c) the heterologous chemokine element is selected from the group consisting of MIP3α, SLC, MDC, MC10, MLP1β, ELC and CCR7, or a homolog thereof.

53. The method of claim 44, wherein
(a) the animal is a rhesus monkey and the recombinant CMV is a recombinant rhCMV;
(b) a viral chemokine element or a viral immune-modulatory gene is disabled, the viral chemokine element selected from the group consisting of rhUS28.1, rhUS28.2; rhUS28.3, rhUS28.4, rhUS28.5, rhUL33 and rhUL78, or a homolog thereof, and the viral immune-modulatory gene selected from the group consisting of rhUL111A, rhUS3, rhUS6, rhUS11, rhUS2, rhUL83 and rhUL40, or a homolog thereof; and
(c) the heterologous chemokine element is selected from the group consisting of MIP3α, SLC, MDC, MC10, MLP1β, ELC and CCR7, or a homolog thereof.

54. The method of claim 44, wherein
(a) the animal is a mouse and the recombinant CMV is a recombinant MCMV;
(b) a viral chemokine element or a viral immune-modulatory gene is disabled, the viral chemokine element selected from the group consisting of MUL33, MUL78, MCK-1 and MCK-2, or a homolog thereof, and the viral immune-modulatory gene selected from the group consisting of m144, m152, m04, m06, m138 or a homolog thereof; and
(c) the heterologous chemokine element is selected from the group consisting of MIP3α, SLC, MDC, MC10, MLP1β, ELC and CCR7, or a homolog thereof.

55. A method of preparing a recombinant CMV, comprising inserting into a CMV genome (i) a first heterologous nucleotide sequence encoding a heterologous chemokine element, and (ii) a second heterologous nucleotide sequence encoding an immunogenic polypeptide, wherein the CMV genome is attenuated.

56. A The method of claim 55, wherein attenuation comprises disabling a viral dissemination gene.

57. The method of claim 56, wherein the viral dissemination gene is a gene encoding a viral chemokine element or a viral immune-modulatory gene.

58. The method of claim 57, wherein
the recombinant CMV is a recombinant human CMV (HCMV) or a recombinant murine CMV(MCMV); and
the viral dissemination gene is a gene encoding a viral chemokine element selected from the group consisting US28, US27, UL33, UL78, UL146, UL147, MCK-1 and MCK-2, or a homolog thereof.

59. The method of claim 57, wherein
the recombinant CMV is a recombinant HCMV or a recombinant MCMV; and
the viral dissemination gene is a viral immune-modulatory gene selected from the group consisting of UL111A, US3, US6, US11, US2, UL83, UL18, UL40, m144, m152, m04, m06 and m138, or a homolog thereof.

60. The method of claim 55, wherein the recombinant CMV has reduced virulence in a host selected from the group consisting of a human, a non-human primate and commercial livestock.

61. The method of claim 55, wherein the recombinant CMV has reduced virulence in a host selected from the group consisting of a rhesus monkey and a mouse.

62. The method of claim 55, wherein the heterologous chemokine element is a mammalian chemokine element.

63. The method of claim 62, wherein the heterologous chemokine element is a chemokine ligand.

64. The method of claim 62, wherein the heterologous chemokine element is a chemokine receptor.

65. The method of claim 62, wherein the heterologous chemokine element is selected from the group consisting of MIP3α, SLC, MDC, MC10, MIP1β, ELC and CCR7, or homolog thereof.

66. The method of claim 55, wherein the immunogenic polypeptide comprises an antigen from a pathogenic organism or a tumor antigen.

67. The method of claim 66, wherein the pathogenic organism is a bacterium, a virus or a parasite.

68. The method of claim 55, further comprising inserting at least one promoter into the CMV genome such that the at least one promoter is operably linked to the first and second heterologous nucleotide sequence.

69. The method of claim 55, further comprising inserting at least two promoters into the CMV genome such that the first and second heterologous nucleotide sequence are operably linked to different promoters.

70. The method of claim 55, further comprising combining the recombinant CMV with a pharmaceutically acceptable carrier, diluent or excipient.

* * * * *

SEQUENCE LISTING

<160> NUMBER OF SEQ ID NOS: 34

<210> SEQ ID NO 1
<211> LENGTH: 1020
<212> TYPE: DNA
<213> ORGANISM: Rhesus cytomegalovirus
<220> FEATURE:
<223> OTHER INFORMATION: rhesus monkey (Macaca mulatta) cytomegalovirus
      (rhCMV) short unique region 28.1 (rhUS28.1) coding
      sequence

<400> SEQUENCE: 1

```
atgaataaca catcttgcaa cttcaacgtc actctcaacg catcggcacc aagccgatac    60
atagctattg ctatgtacag cattgttatc tgtatcgggt tggttggaaa cctgctgtta   120
tgcatcgtgt tagtcaagaa acgcaaactg cgatattcca gcgatgttta ttttttccac   180
gcctctatgg ccgacctcgt cagcactgtc atgctaccgc tctggctaca ttatgtcctc   240
aactttgccc aactctctcg aggagcctgt atcagctttt cggtgacttt ctatgttccc   300
cttttcgttc aggcctggtt actcatttcc atcgctatgg agcgatattc caacttagta   360
tggatggcac ccattagcgt taagacggcc tttaaacact gcataggaac ctggatcgta   420
tctgccttcg tggcatcacc ctactacgca tacagaaact cacacgacga acacgaatgc   480
attctaggaa actacacttg gcacattaac gaaccgctac acacgtgtat ggatgtggtg   540
atcatagtat ggacctttt ggccccagta ctggtaacca ttatagcaag cgtcaaaatg   600
agacgaacga cctggggcaa tactaggtta aacgaaaaga acagcgacat tcttatagta   660
ctagttgtca tgacagtgtt cttttgggga ccgtttaata tcgtgttggt tattgacaat   720
attttacaga gatactatga taccacgaat tgcgatgtag aaaagattaa acatatcatg   780
gctatgatct cagaagccat tgtttatttt cgcggtatta cagcacctat tatttatgta   840
gggattagtg gcagatttcg cgaagagatt tactctctgt ttagacgcca gccgtataac   900
gatttggacc ccgatgccaa tcaattcatg attgaactca ctagccaggg aagaagtaga   960
aatagaaatg ctagacaatc ggaaagcaat gtaccgcaac cagaagaatg cttctggtaa  1020
```

<210> SEQ ID NO 2
<211> LENGTH: 1002
<212> TYPE: DNA
<213> ORGANISM: Rhesus cytomegalovirus
<220> FEATURE:
<223> OTHER INFORMATION: rhesus monkey (Macaca mulatta) cytomegalovirus
      (rhCMV) short unique region 28.2 (rhUS28.2) coding -continued sequence

<400> SEQUENCE: 2

| | | | | |
|---|---|---|---|---|
| atgaccaacg | ccggacactg | tcacataaac | gaaagtctcg | cgtcgtatgg | aatcgctccc | 60 |
| gcagctacca | ttaccttata | cagcattgcg | ggaatctgcg | gtgtcacggg | aaatctgtta | 120 |
| atacttttgg | ttttgttcac | gagacgcata | cactggttcg | caaatgacat | ctactatctc | 180 |
| aacatgatct | ttacagactt | tcttgttttc | attacattac | ccgcctgggt | ttactacctg | 240 |
| ctgaattaca | cacaactctc | acactatgcc | tgcattgctc | tatcatttgt | tttttacgtt | 300 |
| tccattttta | ttcaagctga | ctttatggta | gcagtggcta | tcgagcgtta | tcgaagccta | 360 |
| gtgaaaaaca | aaccccttag | cgtaaaaaaa | gccagcgtca | gctgcgcgtg | catctggatc | 420 |
| attgttatta | tagtgtcttc | accatactac | atgtttagat | cgcaacacga | aacaaattct | 480 |
| tgcattctag | gaaactacac | ctggcatatg | aacagtcctt | tcgcaccac | aatggacgca | 540 |
| tccattaaca | tttggtcttt | tgtcgttccg | gccgtgacga | ccttgttaat | agccagacga | 600 |
| atttatgtat | gtacttcagg | caacaaaaaa | atgaacgcca | gagccagtgg | tttgttagag | 660 |
| gccatggtga | ttagcatgtt | attcttcgga | ggacttttca | acctgaacat | ctttcgagac | 720 |
| atagtttcgg | acacatcgga | agacaataaa | gactgcacat | atcttaagca | ggaacacttt | 780 |
| attcgcatgg | tcggtgtggc | cctcgtttac | gggcgcgcta | tattcaaccc | ttttatgtat | 840 |
| atgtgtgtga | gtaccagatt | gcgccaagaa | ataaaatgtt | tgtttatgcg | aataccttat | 900 |
| gaaacactag | atgcagaaca | cgctaaactc | atggttaatt | taaaaaacag | aaatgctaat | 960 |
| gtacccgatc | ctaaacctcg | tgaatatgaa | tctgtgttat | ag | | 1002 |

<210> SEQ ID NO 3
<211> LENGTH: 1014
<212> TYPE: DNA
<213> ORGANISM: Rhesus cytomegalovirus
<220> FEATURE:
<223> OTHER INFORMATION: rhesus monkey (Macaca mulatta) cytomegalovirus
    (rhCMV) short unique region 28.3 (rhUS28.3) coding
    sequence

<400> SEQUENCE: 3

| | | | | |
|---|---|---|---|---|
| atgaccaaca | ctaacaatac | gacttgtcat | ctcaacggaa | ctttcgaaac | ttttaaaatc | 60 |
| acccgtccag | tagccatcag | cgcctacact | gtactcgtgg | ttatcggact | tttgggaaac | 120 |
| attgtgctgc | tcagcgtgct | cgtcgtgaaa | cgcaagctca | gtttccgaa | tgacatttac | 180 |
| tttttcaacg | cgtctttggc | agacgttttt | gccgtctgca | tgttgcccgc | ctgggttaac | 240 |
| tatgcactga | actccacaca | acttagcaag | ttctcatgta | tcacttttac | gtttggtttt | 300 |
| tacgtctccc | tgttcatcca | ggcctggatg | ctcattctgg | tcaccctgga | gcgatacgga | 360 |
| tctctagtct | ggatcgcccc | gatcaccaga | aacaaagcca | tagcgaattg | tgtactcttt | 420 |
| tggcttgttt | ccatcttctt | ggccgcacct | tactactctt | ttagaaacga | aagcaacgaa | 480 |
| caccaatgca | tcatgagaaa | ctatacctgg | agcgttggtg | aaacatggca | catagccctg | 540 |
| gatttcttaa | ttacgctcat | tacatttatc | atgccagtga | ctattgtgtt | agctctgagt | 600 |
| ttcaaaatgg | ccagatggtc | aacctttggt | tacagaaacc | tcaccagcag | aaccagtctt | 660 |
| atccttattt | tgatactgac | agtagcagca | gggttctggg | gaccttttca | cctatttatg | 720 |
| tttatagaaa | acgtggcagg | gcagatttac | cacattcaaa | aggattgctg | gtacttacag | 780 |
| ctcagacact | tgtgtagctt | gatgaccgaa | acccagtgt | ttctacgttc | agttttttaac | 840 |
| ccttatattt | atatgataat | cagttacaag | tttaggcagc | aggtgcgcag | tctactcaag | 900 |

```
cgtactcagt atgatgcttt ggacacgact cagttagcag aaactatgca gctgaaagcg    960
aaaggtgtgc cggtgtccga ccccgcgccg catgactgcg aatgcttttt gtaa         1014
```

<210> SEQ ID NO 4
<211> LENGTH: 987
<212> TYPE: DNA
<213> ORGANISM: Rhesus cytomegalovirus
<220> FEATURE:
<223> OTHER INFORMATION: rhesus monkey (Macaca mulatta) cytomegalovirus
      (rhCMV) short unique region 28.4 (rhUS28.4) coding
      sequence

<400> SEQUENCE: 4

```
atgaattcga gccagcacaa cataagcgtg tttctctcca ttggagcagg gcccgtcatt     60
accggataca cgtgcgtttt tctgttcggg attctgggac actttactt gtattggaaa    120 aaccatcaga gacgacaccg gacaaacagt ttcagtgatg ttttatttcg acatctcatg    180
atcaccgaag aggtctttac cctcaccatt cccgtctggg cgtatcactt aactactcac    240
ggcaacttac cgggctcgtg gtgccgaagt ctcaccttcg ttttttatct aacggtattc    300
gctcgtgcct tcttttacct gctcctcatc tgggaccgat acagcgtaat catctgcaga    360
caccctctcc ccgttaatct gaactacagt caggtcatag gcctgtctgt ctggctggtt    420
gccgtactgt cagcatcacc gttctccatt tttaacggaa gtgtgaaaca atgcctgggc    480
aacatgggca gcatacccag cgaatcgtct gccgttctta acctggaagt gcacctgtgc    540
tccttctggt taccgctcat catgtcggct aactgttact accaagcaaa acgccgagca    600
tcgcctgacc aactccacga actttaccga tgcagtttgc taattaccat tatcacaact    660
tacgctatcg tatggtttcc tttccatctc gctttactca tagacgccct gattagcata    720
agccatgtag aaccctctag cgctctccac tgggcatcca ttgtcgttac ctgtaaatca    780 tttacattg tatatgcggg cataagccca ctagtgtatt tcacatgctg ccccaccgta    840
cgtcgcgaac tgctgatgtc tctacgtcca ttcttcacct ggatttccag caaaacgcgg    900
cgaggctacg ctccgattaa aacacaacct taaacatcc ccgacgagcc gatagataac    960
aagtcaccgc acctgttaaa cgaataa                                        987
```

<210> SEQ ID NO 5
<211> LENGTH: 1452
<212> TYPE: DNA
<213> ORGANISM: Rhesus cytomegalovirus
<220> FEATURE:
<223> OTHER INFORMATION: rhesus monkey (Macaca mulatta) cytomegalovirus
      (rhCMV) short unique region 28.5 (rhUS28.5) coding
      sequence

<400> SEQUENCE: 5

```
atgactacca ccacaatgag tgctaccacg aattccagta ccacgcctca agcaagcagc     60
accacgatga caacgaagac aagcactcct ggcaatacaa ctactggcac tacgtccacc    120
ctgacaacga tatcaacaac ttctaatgct accagcataa cgtctaattt aagcactacc    180
ggaaaccaaa ctgcaactac caatgctact accttcagtt ccacattaac aacatctaca    240
aatataagca gtcattttc gacagttct accgtcgcat ccaatgcaac atgtaattct    300
acaatcacaa cgaatattac aactgctttt actacagcag caaacactac cgcaagcagc    360
ctcaccagca tcgtaacttc acttgccact accattgaaa ccacatcatt tgattatgat    420
gagtcagcag aagcttgcaa cttaacagac atcgttcata ctactagatc agtgacagtt    480
```

-continued

```
actttctata ctatcatatt catactcggc cttttgggaa actttctggt tcttatgacc      540
atcatttgga accgtcgcat ttcctttatg gttgaaatat atttcgttaa tctagcaatc      600
tccgatctta tgtttgtatg tactttacca ttttggataa tgtatcttct tgagcacgac      660
gtcatgtcac atgcatcctg tgtagcaatg acagccattt tttattgcgc gctgtttgcc      720
agcactgttt tcctcttgct aattgtttta gacagatgtt acgctattct attaggtaca      780
gaaaaagcaa atagacgttt attgcgcaat gctgtttctg gatgcatgct catgtgggga      840
ttgtgtttca ttttagcatt acctcatttt atctttatga agaaaggaac caacgtatgt      900
gtagcagagt atgaaccagg acttaacaat ttctatgtta tttttatcaa tactgaggtg      960
aacctatgca ccctagtttt gccagccgca gccattatct actggtatct taaactaacc     1020
aaagcactca aaacccatga acgactgcgt cataggctaa cgtctctaaa catagtgtta     1080
gctgttgtca ttgtatttgc tttgttttgg ctgccgtata atctcatgct tatgatgtat     1140
agcttagttc acatgcagat accttgggaa tgcagctctg aaaaaatact gagacgaagt     1200
ttaattatta cagaatccat cgccctcagt cactgttgca tcaacccat tatctacttg     1260 ctcttcggac ctcgctgtcg aagcgagttc tgtcacctgt tgcgatgttg ctttacgcgc     1320
ttatgtccac acagatcctg gagttccata cgtgcagaga cggtgtccat cagtctcagt     1380
cactcacagg tatctgcatc atctgaggat gatgacaacg atgtgcatga tgaattgcaa     1440 ttttaattt ga                                                          1452
```

<210> SEQ ID NO 6
<211> LENGTH: 990
<212> TYPE: DNA
<213> ORGANISM: Rhesus cytomegalovirus
<220> FEATURE:
<223> OTHER INFORMATION: rhesus monkey (Macaca mulatta) cytomegalovirus
      (rhCMV) long unique region 33 (rhUL33) coding
      sequence

<400> SEQUENCE: 6

```
atgaccaatc tttactctgc caattttctc accttgatag tacttccttt tatcgtttta       60
agcaatcaac acctttacc tgccagtgca gtaacctgta aatttctctc cctgttgtac      120
tactctagct gcagcgtagg ttttgctaca gtggcactga tagcggccga ccgataccga     180
gtgattcatc gccgaactca agctcgccaa tcctaccgta acacatatat gatagtaggc     240
ttaacgtggc tcattggctt gatctgcgct accccggg gggtctacac aaccattgta       300
gctcaccgcg atggggaaag tgatgctcaa agacacaata cttgcattat gcactttgcg     360
tatgatgaag tttacgtcct catggtctgg aaacttctca tcgttttagt ctggggcata     420
gtgccagttg tcatgatgag ctggttttac gcgtttttt acaatactgt acaaagaaca     480
gccaaaaaac aacaacgtac gttgaaattc gtaaaggtat tactcctgtc attcatcatc     540
atccaaactc cctatgtgtc aatcatgatt tttaacacgt atgccaccgt aggatggccg     600
atggaatgcg ccgatctaac tagacgccga gtcatcaaca cgttttcccg tctcgtcccc     660
aatctacatt gcatggtcaa ccccatcctc tacgctctca tgggaaatga ctttgtgtct     720
aaagtgggcc aatgctttcg gggggaactc acgaaccgtc gaacttttct gcgttccaag     780
caacaagccc gcaactcgga cgatgtaccg acaattgtca gtcaacaacc cgccacaccc     840
accatcgtca ataagcccga aaaaaacccg cacgtaaaac gcggtgtatc tttcagcgtc     900
agcgcatctt ccgaactcgc agcggccaaa aaagccaaag acaaagccaa gcggctttcc     960
atgtcccacc aaaacctacg tctgacgtga                                      990
```

<210> SEQ ID NO 7
<211> LENGTH: 1328
<212> TYPE: DNA
<213> ORGANISM: Rhesus cytomegalovirus
<220> FEATURE:
<223> OTHER INFORMATION: rhesus monkey (Macaca mulatta) cytomegalovirus
(rhCMV) long unique region 33 (rhUL33) spliced
coding sequence

<400> SEQUENCE: 7

| | | | | | |
|---|---|---|---|---|---|
| atggcagtca | ctttacgagg | cggcagcccg | ataaacttta | aactcatgat | tgtcagccac | 60 |
| agaaaccgga | aatttcacga | gatacggctg | tttcagcgtt | ctgctatccg | tccaggcggg | 120 |
| ttatggaaac | cattcttcac | aaccgaacga | gtgaaactaa | ttccattttg | cacatcaaca | 180 |
| ccacctgcaa | tgtgaccgac | tcactgtacg | ccgccaaact | aggcgaagcc | ctcgtgaaca | 240 |
| gcgcgctagc | tttattcggt | accccctca | acgccatcgt | cctcgtcaca | cagctattgg | 300 |
| ccaaccgagt | tcatggatac | tccaccccga | ttatctacat | gaccaatctt | tactctgcca | 360 |
| attttctcac | cttgatagta | cttcctttta | tcgttttaag | caatcaacac | cttttacctg | 420 |
| ccagtgcagt | aacctgtaaa | tttctctccc | tgttgtacta | ctctagctgc | agcgtaggtt | 480 |
| ttgctacagt | ggcactgata | gcggccgacc | gataccgagt | gattcatcgc | cgaactcaag | 540 |
| ctcgccaatc | ctaccgtaac | acatatatga | tagtaggctt | aacgtggctc | attggcttga | 600 |
| tctgcgctac | ccccggggg | gtctacacaa | ccattgtagc | tcaccgcgat | ggggaaagtg | 660 |
| atgctcaaag | acacaatact | tgcattatgc | actttgcgta | tgatgaagtt | tacgtcctca | 720 |
| tggtctggaa | acttctcatc | gttttagtct | ggggcatagt | gccagttgtc | atgatgagct | 780 |
| ggttttacgc | gttttttac | aatactgtac | aaagaacagc | caaaaacaa | caacgtacgt | 840 |
| tgaaattcgt | aaaggtatta | ctcctgtcat | tcatcatcat | ccaaactccc | tatgtgtcaa | 900 |
| tcatgatttt | taacacgtat | gccaccgtag | gatggccgat | ggaatgcgcc | gatctaacta | 960 |
| gacgccgagt | catcaacacg | ttttcccgtc | tcgtccccaa | tctacattgc | atggtcaacc | 1020 |
| ccatcctcta | cgctctcatg | ggaaatgact | ttgtgtctaa | agtgggccaa | tgctttcggg | 1080 |
| gggaactcac | gaaccgtcga | acttttctgc | gttccaagca | acaagcccgc | aactcggacg | 1140 |
| atgtaccgac | aattgtcagt | caacaacccg | ccacacccac | catcgtcaat | aagcccgaaa | 1200 |
| aaaacccgca | cgtaaaacgc | ggtgtatctt | tcagcgtcag | cgcatcttcc | gaactcgcag | 1260 |
| cggccaaaaa | agccaaagac | aaagccaagc | ggctttccat | gtcccaccaa | aacctacgtc | 1320 |
| tgacgtga | | | | | | 1328 |

<210> SEQ ID NO 8
<211> LENGTH: 1140
<212> TYPE: DNA
<213> ORGANISM: Rhesus cytomegalovirus
<220> FEATURE:
<223> OTHER INFORMATION: rhesus monkey (Macaca mulatta) cytomegalovirus
(rhCMV) long unique region 78 (rhUL78) coding
sequence

<400> SEQUENCE: 8

| | | | | | |
|---|---|---|---|---|---|
| atgattacgg | agcgcgtcct | cgcaggcatc | ctcgcgggca | tgacggccgc | ggggagtttg | 60 |
| gtcattctcc | tcgcggttgt | tatgtggttg | aacatgttag | atcgcgctgg | catgccaatg | 120 |
| gccgttgggc | attacacagg | gaacctggtg | ttgactcagg | tcatctgtat | cttctccatg | 180 |
| ctggcgtcta | aaattgttgg | catgacgagt | gcggccaaca | tgggcttctg | cggcatcgtg | 240 |

-continued

```
gtttttctgg aagacactgg cctctatgtc acctcgctgc tcttcatgtt tatgatcctg      300
gatcgcatgg cggctttttct taacgggcgt cttttctgga ggcagcagac gacgaagcag    360
aatctgagta caagcgtgta cattattctg ttttgctggg tgttgggaat ggccgcggct    420
gttcccagcg cggctgtggc tgcacccaat tccaggtggg aacgctgcga aattccagtg    480
tcatatgccg caatcgacat gattgtgaag ctctggtttg tgctgttggc acccgtcgtg    540
ctgattatgg ctgtgatcat tcaatcttcc tatcatcgtg atcgggagag gatctggtac    600
tatgccagac gtgtgttcat gttctacacg gcctgctttg tcatgatggt gccttattac    660
ttcgtcagag tcatgctgag cgactttgct ttggttgata aaaaacaaa aacggcgaac      720 agcgacggtt gtgattcgac atttcttgat tatctgaaca tgttcactca cgtgatttac     780
agttttaagt tggtggtgtt tgctttgttc attgtcctgt tttgctccat aaacccgatg    840
gaaacgctgg aagaatgctt ggagagggcc gatgctgaga ggcaaagtcg gtcagaagca    900
tcccagggtg aaaggaggct gccaatcaac acatgctgta taagttgat tgaattgata    960 aagcagtatg taagcactct ctctaaagcc acgagggaca attctggcga aagggccaat    1020
ttgccagaga atgctgaaga tattggaaca actggcagtg atcagctacc gactgaggtc    1080
accgtgaccc caaattcatc ggctgtgttt agcactggag gaacggtgtc tccagtctaa    1140
```

<210> SEQ ID NO 9
<211> LENGTH: 2100
<212> TYPE: DNA
<213> ORGANISM: Rhesus cytomegalovirus
<220> FEATURE:
<223> OTHER INFORMATION: rhesus monkey (Macaca mulatta) cytomegalovirus
      (rhCMV) long unique region 33 (rhUL33) splice
      variant segment that extends 1000 nucleotides
      upstream and 200 nucleotides downstream of the
      rhUL33 reading frame
<220> FEATURE:
<221> NAME/KEY: exon
<222> LOCATION: (603)..(752)
<223> OTHER INFORMATION: exon 1
<220> FEATURE:
<221> NAME/KEY: intron
<222> LOCATION: (753)..(830)
<220> FEATURE:
<221> NAME/KEY: exon
<222> LOCATION: (831)..(2006)
<223> OTHER INFORMATION: exon 2
<220> FEATURE:
<221> NAME/KEY: misc_feature
<222> LOCATION: (1017)..(2006)
<223> OTHER INFORMATION: unspliced gene

<400> SEQUENCE: 9

```
cggccaagat gtcccaagag gttctgacat gaacaatcac ttttccgaga tagatgagtt     60
tgttagtggc atttaccaga gaactattgg agtgacgctc aagatgaagc ttcactggcc    120
gtatttcgaa catattgtta gatatagcta gtaaagaatc ttctaaagcc atgacgtctt    180
tctgacgaag ttgaataaat tctatctcac cagtacccaa aggctgacac tcagacaact    240
ttgccaaggc cgttgcaccc accatggcat tctgaatcac agtaacatcc gtccgagaat    300
cgtcaccaaa aacggtggcc tccaaagttc gcaggtgagg ccgagccttt actggatctc    360
ggaagggata catgtgtgct cgccgagtga cagcattagc attaacctca aactcatcta    420
aaagcgatga taaatcagga atatgatagc gcaattctcg atagtaggcc aaccagagga    480
ctaattggtt gaacagacag ctccgtctgt gcaaaaactt ttcgccgcat tttctgagaa    540
ttttaggatg ctgctctaaa tctacgttct ctttagtcgg cagggtcttt aaaagttag    600
```

-continued

```
tgatggcagt cactttacga ggcggcagcc cgataaactt taaactcatg attgtcagcc    660
acagaaaccg gaaatttcac gagatacggc tgtttcagcg ttctgctatc cgtccaggcg    720
ggttatggaa accattcttc acaaccgaac ggtgagtgac atttaagaca gtttaatagc    780
caacactcgt aacgtctcgg aagctgataa gtttcgtttt tccacagagt gaaactaatt    840
ccattttgca catcaacacc acctgcaatg tgaccgactc actgtacgcc gccaaactag    900
gcgaagccct cgtgaacagc gcgctagctt tattcggtac ccccctcaac gccatcgtcc    960
tcgtcacaca gctattggcc aaccgagttc atggatactc caccccgatt atctacatga   1020 ccaatctta ctctgccaat tttctcacct tgatagtact tccttttatc gttttaagca   1080
atcaacacct tttacctgcc agtgcagtaa cctgtaaatt tctctccctg ttgtactact   1140
ctagctgcag cgtaggtttt gctacagtgg cactgatagc ggccgaccga taccgagtga   1200
ttcatcgccg aactcaagct cgccaatcct accgtaacac atatatgata gtaggcttaa   1260
cgtggctcat tggcttgatc tgcgctaccc ccggggggt ctacacaacc attgtagctc    1320
accgcgatgg ggaaagtgat gctcaaagac acaatacttg cattatgcac tttgcgtatg   1380
atgaagttta cgtcctcatg gtctggaaac ttctcatcgt tttagtctgg ggcatagtgc   1440
cagttgtcat gatgagctgg ttttacgcgt tttttacaa tactgtacaa agaacagcca    1500 aaaacaaca acgtacgttg aaattcgtaa aggtattact cctgtcattc atcatcatcc    1560
aaactcccta tgtgtcaatc atgattttta acacgtatgc caccgtagga tggccgatgg   1620
aatgcgccga tctaactaga cgccgagtca tcaacacgtt ttcccgtctc gtccccaatc   1680
tacattgcat ggtcaacccc atcctctacg ctctcatggg aaatgacttt gtgtctaaag   1740
tgggccaatg ctttcggggg gaactcacga accgtcgaac ttttctgcgt tccaagcaac   1800
aagcccgcaa ctcggacgat gtaccgacaa ttgtcagtca acaacccgcc acacccacca   1860
tcgtcaataa gcccgaaaaa aacccgcacg taaaacgcgg tgtatctttc agcgtcagcg   1920
catcttccga actcgcagcg gccaaaaaag ccaaagacaa agccaagcgg ctttccatgt   1980
cccaccaaaa cctacgtctg acgtgaattt tcctagaggc tgcctccacg ggtttacata   2040
catatctcgg tacttgctac acttgatcac tttactgcgg acaccacggc caatcgcatc   2100
```

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:human
      cytomegalovirus (HCMV) long unique region 146
      (UL146) CXC (alpha) chemokine homolog (vCXC1)
      clinical strain conserved structural motif
<220> FEATURE:
<221> NAME/KEY: MOD_RES
<222> LOCATION: (5)
<223> OTHER INFORMATION: Xaa = any amino acid

<400> SEQUENCE: 10

Glu Leu Arg Cys Xaa Cys
 1               5

<210> SEQ ID NO 11
<211> LENGTH: 26
<212> TYPE: DNA
<213> ORGANISM: Artificial Sequence
<220> FEATURE:
<223> OTHER INFORMATION: Description of Artificial Sequence:human CMV
      strain AD 169 AD27/28 PCR amplification primer
      AD27up

<400> SEQUENCE: 11
gtgaattcgg ttggttcccc gtgttt                                              26

<210> SEQ ID NO 12
<211> LENGTH: 32
<212> TYPE: DNA
<213> ORGANISM: Artificial Sequence
<220> FEATURE:
<223> OTHER INFORMATION: Description of Artificial Sequence:human CMV
      strain AD169 AD27/28 PCR amplification primer
      AD28low

<400> SEQUENCE: 12
gcggatcctc gcgagtcgcg tcttcatcgt ag                                       32

<210> SEQ ID NO 13
<211> LENGTH: 31
<212> TYPE: DNA
<213> ORGANISM: Artificial Sequence
<220> FEATURE:
<223> OTHER INFORMATION: Description of Artificial Sequence:human CMV
      strain AD169 AD27/28 PCR amplification primer
      AD28up

<400> SEQUENCE: 13
gtggatcctc gagcgctcgc cttttgtcac t                                        31

<210> SEQ ID NO 14
<211> LENGTH: 26
<212> TYPE: DNA
<213> ORGANISM: Artificial Sequence
<220> FEATURE:
<223> OTHER INFORMATION: Description of Artificial Sequence:human CMV
      strain AD169 AD27/28 PCR amplification primer
      AD29low

<400> SEQUENCE: 14
gcggatcccc ccgcccacca tacaac                                              26

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence:human CCR7
      receptor CCR7.1 PCR amplification primer ccr7up

<400> SEQUENCE: 15
gcgaattcag cgtcatggac ctgggg                                              26

<210> SEQ ID NO 16
<211> LENGTH: 26
<212> TYPE: DNA
<213> ORGANISM: Artificial Sequence
<220> FEATURE:
<223> OTHER INFORMATION: Description of Artificial Sequence:human CCR7
      receptor CCR7.1 PCR amplification primer ccr7low

<400> SEQUENCE: 16
tggaattcag aagagtcgcc tatggg                                              26

<210> SEQ ID NO 17
<211> LENGTH: 34
<212> TYPE: DNA
<213> ORGANISM: Artificial Sequence
<220> FEATURE:

```
<223> OTHER INFORMATION: Description of Artificial Sequence:murine CMV
      PCR amplification primer S78.1

<400> SEQUENCE: 17
ataagaatgc ggccgctcga ctacatgctg ctgc                                    34

<210> SEQ ID NO 18
<211> LENGTH: 30
<212> TYPE: DNA
<213> ORGANISM: Artificial Sequence
<220> FEATURE:
<223> OTHER INFORMATION: Description of Artificial Sequence:murine CMV
      PCR amplification primer S78.2

<400> SEQUENCE: 18
cggaattccg tccggctgct gcgcttcttc                                         30

<210> SEQ ID NO 19
<211> LENGTH: 35
<212> TYPE: DNA
<213> ORGANISM: Artificial Sequence
<220> FEATURE:
<223> OTHER INFORMATION: Description of Artificial Sequence:murine CCR7
      receptor (mCCR7) PCR amplification primer mCCR7up

<400> SEQUENCE: 19
ataagaatgc ggccgctgac ccagggaaac ccagg                                   35

<210> SEQ ID NO 20
<211> LENGTH: 33
<212> TYPE: DNA
<213> ORGANISM: Artificial Sequence
<220> FEATURE:
<223> OTHER INFORMATION: Description of Artificial Sequence:murine CCR7
      receptor (mCCR7) PCR amplification primer mCCR7low

<400> SEQUENCE: 20
cggaattccg tcagctcctg ggagaggtcc ttg                                     33

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence:human CMV
      strain AD169 PCR amplification primer 108 up

<400> SEQUENCE: 21
gcggtaccgc gacgccgtcg ctggg                                              25

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:human CMV
      strain AD169 PCR amplification primer 108 low

<400> SEQUENCE: 22
tggatccgtc agggaaatac aag                                                23

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence:human CMV
``` strain AD169 PCR amplification primer 109 up

<400> SEQUENCE: 23
atggatcctc ttctatcacg gtggc                                          25

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence:human CMV
      strain AD169 PCR amplification primer 109 low

<400> SEQUENCE: 24
gcggatccag gatcgatttc gtgcg                                          25

<210> SEQ ID NO 25
<211> LENGTH: 28
<212> TYPE: DNA
<213> ORGANISM: Artificial Sequence
<220> FEATURE:
<223> OTHER INFORMATION: Description of Artificial Sequence:Bacillus
      anthracis protective antigen (BAPA) PCR primer
      BAPAup

<400> SEQUENCE: 25
ggcccgggga agttaaacag gagaaccg                                       28

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence:Bacillus
      anthracis protective antigen (BAPA) PCR primer
      BAPAlow

<400> SEQUENCE: 26
gggatatctt accttatcct atctcat                                        27

<210> SEQ ID NO 27
<211> LENGTH: 70
<212> TYPE: DNA
<213> ORGANISM: Artificial Sequence
<220> FEATURE:
<223> OTHER INFORMATION: Description of Artificial Sequence:comple-
      mentary oligo containing Ig kappa leader sequence

<400> SEQUENCE: 27
ctagcatgga gacagacaca ctcctgctat gggtactgct gctctgggtt ccaggttcca    60
ctggtgaccc                                                           70

<210> SEQ ID NO 28
<211> LENGTH: 70
<212> TYPE: DNA
<213> ORGANISM: Artificial Sequence
<220> FEATURE:
<223> OTHER INFORMATION: Description of Artificial Sequence:
      complementary oligo containing Ig kappa leader sequence

<400> SEQUENCE: 28
ccgggggtca ccagtggaac ctggaaccca gagcagcagt acccatagca ggagtgtgtc    60
tgtctccatg                                                           70

<210> SEQ ID NO 29

```
<211> LENGTH: 29
<212> TYPE: DNA
<213> ORGANISM: Artificial Sequence
<220> FEATURE:
<223> OTHER INFORMATION: Description of Artificial Sequence:rhesus CMV
      strain Rh68.1 Rh32/33 PCR amplification primer
      Rh32up

<400> SEQUENCE: 29
cggaattcct ctttagtcgg cagggtctt                                      29

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence:rhesus CMV
      strain Rh68.1 Rh32/33  PCR amplification primer
      Rh33low

<400> SEQUENCE: 30
ctggatccgt ggctttgtct ttggctttt                                      29

<210> SEQ ID NO 31
<211> LENGTH: 28
<212> TYPE: DNA
<213> ORGANISM: Artificial Sequence
<220> FEATURE:
<223> OTHER INFORMATION: Description of Artificial Sequence:rhesus
      macaque SLO RhCMV immediate early 2 gene nested PCR primer

<400> SEQUENCE: 31
gccaatgcat cctctggatg tattgtga                                       28

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence:rhesus
      macaque SLO RhCMV immediate early 2 gene nested PCR primer

<400> SEQUENCE: 32
tgcttgggga atctctgcac                                                20

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence:rhesus
      macaque SLO RhCMV immediate early 2 gene nested PCR primer

<400> SEQUENCE: 33
cccttcctga ctactaatgt ac                                             22

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence:rhesus
      macaque SLO RhCMV immediate early 2 gene nested PCR primer

<400> SEQUENCE: 34
ttggggaatc tctgcacaag                                                20
```